(12) United States Patent
Kovach

(10) Patent No.: US 10,149,847 B2
(45) Date of Patent: Dec. 11, 2018

(54) OXABICYCLOHEPTANES AND OXABICYCLOHEPTENES FOR THE TREATMENT OF DIABETES

(71) Applicant: Lixte Biotechnology, Inc., East Setauket, NY (US)

(72) Inventor: John S. Kovach, East Setauket, NY (US)

(73) Assignee: Lixte Biotechnology, Inc., Setauket, NY (US)

( * ) Notice: Subject to any disclaimer, the term of this patent is extended or adjusted under 35 U.S.C. 154(b) by 162 days.

(21) Appl. No.: 14/408,475

(22) PCT Filed: Jun. 28, 2013

(86) PCT No.: PCT/US2013/048703
§ 371 (c)(1),
(2) Date: Dec. 16, 2014

(87) PCT Pub. No.: WO2014/005084
PCT Pub. Date: Jan. 3, 2004

(65) Prior Publication Data
US 2015/0148353 A1    May 28, 2015

Related U.S. Application Data

(60) Provisional application No. 61/666,552, filed on Jun. 29, 2012.

(51) Int. Cl.
| | |
|---|---|
| *A61K 31/496* | (2006.01) |
| *C07D 493/08* | (2006.01) |
| *A61K 31/34* | (2006.01) |
| *A61K 31/4178* | (2006.01) |
| *A61K 31/4525* | (2006.01) |

(52) U.S. Cl.
CPC ............ *A61K 31/496* (2013.01); *A61K 31/34* (2013.01); *A61K 31/4178* (2013.01); *A61K 31/4525* (2013.01); *C07D 493/08* (2013.01)

(58) Field of Classification Search
CPC .................................................. A61K 31/496
See application file for complete search history.

(56) References Cited

U.S. PATENT DOCUMENTS

| | | | |
|---|---|---|---|
| 7,998,957 B2 | 8/2011 | Kovach et al. | |
| 8,058,268 B2 | 11/2011 | Kovach | |
| 8,143,445 B2 | 3/2012 | Kovach et al. | |
| 8,227,473 B2 | 7/2012 | Kovach et al. | |
| 8,329,719 B2 | 12/2012 | Kovach | |
| 8,426,444 B2 | 4/2013 | Kovach et al. | |
| 8,455,688 B2 | 6/2013 | Kovach et al. | |
| 8,541,458 B2 * | 9/2013 | Johnson et al. | ... A61K 31/4178 514/389 |
| 8,822,451 B2 | 9/2014 | Kovach et al. | |
| 9,079,917 B2 | 7/2015 | Kovach et al. | |
| 9,526,915 B2 | 12/2016 | Kovach | |
| 9,833,450 B2 | 12/2017 | Kovach et al. | |
| 2009/0264496 A1 | 10/2009 | Vafai et al. | |
| 2010/0029683 A1* | 2/2010 | Zhuang | ................... A61K 31/34 514/254.11 |
| 2011/0286930 A1* | 11/2011 | Tissenbaum | ....... G01N 33/5041 424/9.2 |
| 2015/0174123 A1 | 6/2015 | Kovach | |
| 2016/0051544 A1 | 2/2016 | Kovach et al. | |
| 2016/0074390 A1 | 3/2016 | Kovach | |
| 2016/0264593 A1 | 9/2016 | Kovach et al. | |
| 2016/0303115 A1 | 10/2016 | Kovach et al. | |
| 2016/0333024 A1 | 11/2016 | Kovach | |
| 2017/0136008 A1 | 5/2017 | Kovach et al. | |
| 2017/0259081 A1 | 9/2017 | Kovach et al. | |
| 2017/0369503 A1 | 12/2017 | Kovach et al. | |

FOREIGN PATENT DOCUMENTS

| | | |
|---|---|---|
| WO | WO 2007/092414 A1 | 8/2007 |
| WO | WO 2008/097561 A1 | 8/2008 |
| WO | WO 2009/020565 A1 | 2/2009 |
| WO | WO 2009/045440 A1 | 4/2009 |
| WO | WO 2010/014141 A1 | 2/2010 |

(Continued)

OTHER PUBLICATIONS

Ugi, S., et al. "Protein Phosphatase 2A Negatively Regulates Insulin's Metabolic Signaling Pathway by Inhibiting Akt (Protein Kinase B) Activity in 3T3-L1 Adipocytes." Molecular & Cellular Biology. (Oct. 2004), vol. 24, No. 19, pp. 8778-8789.*
Davis, S.N., et al. "Clarifying the Role of Insulin in Type 2 Diabetes Management." Clinical Diabetes. (2003), vol. 21, No. 1, pp. 14-21.*
Friedman, J.E., et al. "Decreased Akt kinase activity and insulin resistance in C57BL/KsJ-Leprdb/db mice." Journal of Endocrinology. (2000), vol. 167, pp. 107-115.*
Notification of Transmittal of the International Search Report and the Written Opinion of the International Searching Authority, or the Declaration, including an International Search Report and Written Opinion of the International Searching Authority, dated Dec. 3, 2013 in connection with PCT International Application No. PCT/US2013/048703, filed Jun. 28, 2013.
International Search Report dated Dec. 3, 2013 in connection with PCT International Application No. PCT/US2013/048703.

(Continued)

*Primary Examiner* — Andrew D Kosar
*Assistant Examiner* — John S Kenyon
(74) *Attorney, Agent, or Firm* — Andrea L. C. Reid; Dechert LLP

(57) ABSTRACT

A method of increasing the insulin sensitivity of a mammalian cell by contacting the cell with a protein phosphatase 2A (PP2A) inhibitor having the structure:

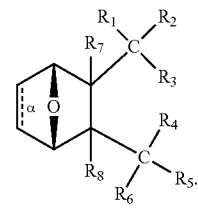

20 Claims, No Drawings

(56) References Cited

FOREIGN PATENT DOCUMENTS

| WO | WO 2010/014220 A1 | 2/2010 | |
|---|---|---|---|
| WO | WO 2010/014254 A1 | 2/2010 | |
| WO | WO 2010/147612 A1 | 12/2010 | |
| WO | WO 2012/162535 A1 | 11/2012 | |
| WO | WO2012162535 | * 11/2012 | |
| WO | WO 2012162535 A1 * | 11/2012 | ........... A61K 31/343 |
| WO | WO 2014/005080 A1 | 1/2014 | |
| WO | WO 2014/005084 A1 | 1/2014 | |
| WO | WO 2014/137741 A1 | 9/2014 | |
| WO | WO 2014/149494 A1 | 9/2014 | |
| WO | WO 2014/168941 A1 | 10/2014 | |
| WO | WO 2015/073802 A1 | 5/2015 | |
| WO | WO 2015/196073 A1 | 12/2015 | |
| WO | WO 2016/014783 A1 | 1/2016 | |
| WO | WO 2016/040877 A1 | 3/2016 | |
| WO | WO 2016/061193 A1 | 4/2016 | |
| WO | WO 2016/134257 A1 | 8/2016 | |
| WO | WO 2016/186963 A1 | 11/2016 | |

OTHER PUBLICATIONS

Written Opinion of the International Searching Authority dated Dec. 3, 2013 in connection with PCT International Application No. PCT/US2013/048703.

International Preliminary Report on Patentability dated Dec. 31, 2014 in connection with PCT International Application PCT/2013/048703.

European Search Report dated Nov. 19, 2015 in connection with European Patent Application No. 13809895.9.

Giovannucci, E. (2010) Diabetes and Cancer: a Consensus Report. Diabetes Care, vol. 33, No. 7, pp. 1674-1685.

Amendment filed Jun. 17, 2016 dated Nov. 19, 2015 in connection with European Patent Application No. 13809895.9.

Du et al., "PP2A contributes to endothelial death in high glucose: inhibition by benfotiamine," American Journal Physiology Regulatory, Integrative and Comparative Physiology, vol. 299, No. 6, Dec. 2010 (pp. R1610-R1617).

Galbo et al., "Free Fatty Acid-Induced PP2A Hyperactivity Selectively Impairs Hepatic Insulin Action on Glucose Metabolism," PLoS One, vol. 6, No. 11, Nov. 2011 (9 pages).

Han et al., "Ascorbate protects endothelial banier function during septic insult: Role of protein phosphatase type 2A," Free Radical Biology and Medicine, vol. 48, No. 1, Jan. 2010 (pp. 128-135).

Kowluru et al., "Hyperactivation of protein phosphatase 2A in models of glucolipotoxicity and diabetes: potential mechanisms and functional consequences," Biochemical Pharmacology, vol. 84, No. 5, Sep. 2012 (pp. 591-597).

Ladurner et al., "Ascorbate stimulates endothelial nitric oxide synthase enzyme activity by rapid modulation of its phosphorylation status," Free Radical Biology and Medicine, vol. 52, No. 10, May 2012 (pp. 2082-2090).

Lu et al., "Inhibition of serine/threonine phosphatase PP2A enhances cancer chemotherapy by blocking DNA damage induced defense mechanisms," Proceedings of the National Academy of Sciences, U.S.A., vol. 106, No. 28, Jul. 2009 (pp. 11697-11702).

May et al., "Nitric Oxide Mediates Tightening of the Endothelial Barrier by Ascorbic Acid," Biochemical and Biophysical Research Communications, vol. 404, No. 2, Jan. 2011 (pp. 701-705).

Wu et al., "Activation of Protein Phosphatase 2A by Palmitate Inhibits AMP-activated Protein Kinase," Journal of Biological Chemistry, vol. 282, No. 13, Mar. 2007 (pp. 9777-9788).

Wu et al., "Peroxynitrite-dependent activation of protein phosphatase type 2A mediates microvascular endothelial barrier dysfunction," Cardiovascular Research, vol. 81, No. 1, Jan. 2009 (pp. 38-45).

Zhou et al., "Ascorbate protects against vascular leakage in cecal ligation and puncture-induced septic peritonitis," American Journal Physiology Regulatory, Integrative and Comparative Physiology, vol. 302, No. 2, Feb. 2012 (pp. R409-R416).

Hojlund et al., "Effect of insulin on protein phosphatase 2A expression in muscle in type 2 diabetes," European Journal of Clinical Investigation, vol. 32, No. 12, Dec. 2002 (pp. 918-923).

* cited by examiner

OXABICYCLOHEPTANES AND OXABICYCLOHEPTENES FOR THE TREATMENT OF DIABETES

CROSS-REFERENCE TO RELATED APPLICATIONS

This application is a § 371 national stage of PCT International Application No. PCT/US2013/048703, filed Jun. 28, 2013, claiming the benefit of U.S. Provisional Application No. 61/666,552, filed Jun. 29, 2012, the contents of each of which are hereby incorporated by reference in their entirety.

Throughout this application various publications are referenced. The disclosures of these documents in their entireties are hereby incorporated by reference into this application in order to more fully describe the state of the art to which this invention pertains.

BACKGROUND OF THE INVENTION

Diabetes mellitus (diabetes) is a complex chronic disease characterized by high levels of blood glucose resulting from defects in insulin secretion and/or insulin action. In order to function properly, the human body must have a balanced production of insulin from the pancreas to transport glucose efficiently to other organs and tissues for storage. Any insulin imbalance or loss of sensitivity can cause a chronic overabundance of glucose leading to diabetes.

Diabetes is associated with various, and often serious complications that may lead premature death. Diabetics are more likely to suffer from heart disease, kidney disease, eye disease including blindness, peripheral vascular disease at times requiring amputation of the leg, stroke, and are more likely to die of complications of flu and pneumonia than non-diabetics. Other conditions related to diabetes include nervous system diseases, which often includes impaired sensation or pain in the feet or hands, slowed digestion of food in the stomach, carpal tunnel syndrome, periodontal disease, and complications of pregnancy, diabetic ketoacidosis and hyperosmolar nonketotic coma.

Type 2 diabetes, in particular, is one of the major medical problems facing populations throughout the world. In the United States, approximately 15% of the adult population is believed to have type 2 diabetes. This incidence is steadily increasing. It has recently been reported that even children are now being diagnosed with type 2 diabetes, a phenomenon that has almost been unheard of in the past. In type 2 diabetes, the ability of insulin to decrease blood glucose levels is impaired and overcoming this insulin resistance is a major goal in type 2 diabetes.

Insulin resistance is a physiological condition where the natural hormone insulin, a hormone made by the pancreas, becomes less effective at regulating blood glucose levels. As blood glucose level rises after a meal, the pancreas releases insulin to help cells take in and use the glucose. Insulin resistance disrupts this process as muscle and fat cells fail to respond adequately to the circulating insulin. As a result, the body requires additional insulin to help facilitate glucose entry into the cells. In response to the increased demand, the pancreas then produces additional insulin. However, the pancreas eventually fails to produce enough insulin to satisfy the body's needs. The result is high levels of insulin and excess glucose in the bloodstream.

SUMMARY OF THE INVENTION

A method of increasing the insulin sensitivity of a mammalian cell by contacting the cell with a protein phosphatase 2A (PP2A) inhibitor having the structure:

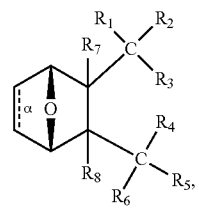

wherein bond α is present or absent;

$R_1$ and $R_2$ is each independently H, O⁻ or $OR_9$, where $R_9$ is H, alkyl, alkenyl, alkynyl or aryl, or $R_1$ and $R_2$ together are =O;

$R_3$ and $R_4$ are each different, and each is OH, O⁻, $OR_9$, $OR_{10}$, $O(CH_2)_{1-6}R_9$, SH, S⁻, $SR_9$,

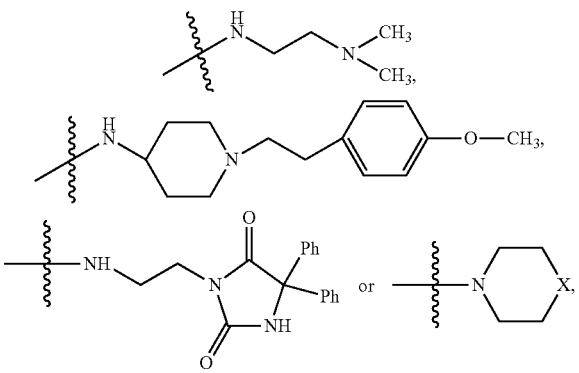

where x is O, S, $NR_{10}$, or $N^+R_{10}R_{10}$, where each $R_{10}$ is independently H, alkyl, $C_2$-$C_{12}$ alkenyl, $C_4$-$C_{12}$ alkenyl, alkynyl, aryl, substituted aryl where the substituent is other than chloro when $R_1$ and $R_2$ are =O,

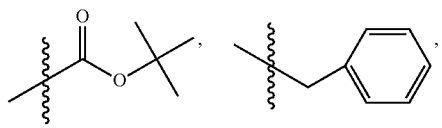

—$CH_2CN$, —$CH_2CO_2R_{11}$, —$CH_2COR_{11}$, —$NHR_{11}$ or —$NH(R_{11})_2$, wherein each $R_{11}$ is independently alkyl, alkenyl or alkynyl, or H;

$R_5$ and $R_6$ is each independently H, OH, or $R_5$ and $R_6$ taken together are =O;

$R_7$ and $R_8$ is each independently H, F, Cl, Br, $SO_2Ph$, $CO_2CH_3$, or $SR_{12}$, where $R_{12}$ is H, alkyl, alkenyl, alkynyl or aryl; and each occurrence of alkyl, alkenyl, or alkynyl is branched or unbranched, unsubstituted or substituted, or a salt, enantiomer or zwitterion of the compound.

A method of treating Type 2 Diabetes in a subject afflicted with Type 2 Diabetes comprising administering to the subject a therapeutically effective amount of a protein phosphatase 2A inhibitor having the structure:

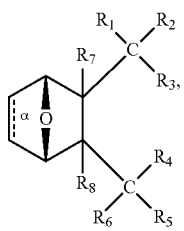

wherein
bond α is present or absent;
$R_1$ and $R_2$ is each independently H, O$^-$ or OR$_9$,
where $R_9$ is H, alkyl, alkenyl, alkynyl or aryl,
or $R_1$ and $R_2$ together are =O;
$R_3$ and $R_4$ are each different, and each is OH, O$^-$, OR$_9$, OR$_{10}$, O(CH$_2$)$_{1-6}$R$_9$, SH, S$^-$, SR$_9$,

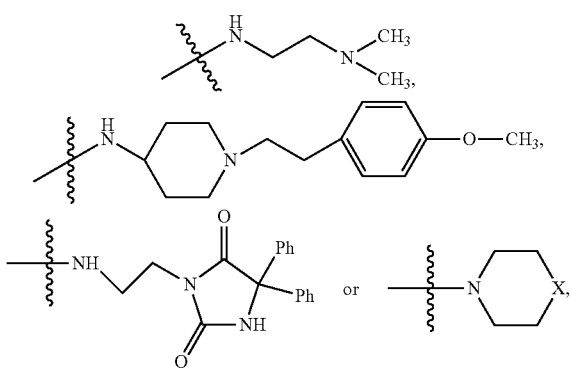

where X is O, S, NR$_{10}$, or N$^+$R$_{10}$R$_{10}$,
where each R$_{10}$ is independently H, alkyl, C$_2$-C$_{12}$alkyl, alkenyl, C$_4$-C$_{12}$ alkenyl, alkynyl, aryl, substituted aryl where the substituent is other than chloro when $R_1$ and $R_2$ are =O,

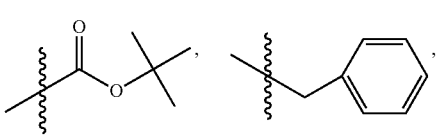

—CH$_2$CN, —CH$_2$CO$_2$R$_{11}$, —CH$_2$COR$_{11}$, —NHR$_{11}$ or —NH$^+$(R$_{11}$)$_2$,
wherein each R$_{11}$ is independently alkyl, alkenyl or alkynyl, or H;
$R_5$ and $R_6$ is each independently H, OH, or $R_5$ and $R_6$ taken together are =O;
$R_7$ and $R_8$ is each independently H, F, Cl, Br, SO$_2$Ph, CO$_2$CH$_3$, or SR$_{12}$,
where R$_{12}$ is H, alkyl, alkenyl, alkynyl or aryl; and
each occurrence of alkyl, alkenyl, or alkynyl is branched or unbranched, unsubstituted or substituted,
or a salt, enantiomer or zwitterion of the compound.

A method of reducing complications associated with Type 2 Diabetes in a subject afflicted with Type 2 Diabetes comprising administering to the subject a therapeutically effective amount of a protein phosphatase 2A inhibitor having the structure:

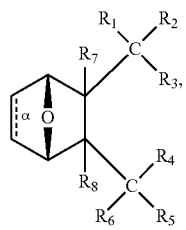

wherein
bond α is present or absent;
$R_1$ and $R_2$ is each independently H, O$^-$ or OR$_9$,
where $R_9$ is H, alkyl, alkenyl, alkynyl or aryl,
or $R_1$ and $R_2$ together are =O;
$R_3$ and $R_4$ are each different, and each is OH, O$^-$, OR$_9$, OR$_{10}$, O(CH$_2$)$_{1-6}$R$_9$, SH, S$^-$, SR$_9$,

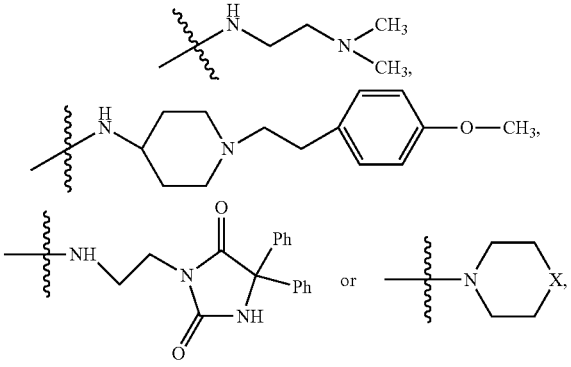

where X is O, S, NR$_{10}$, or N$^+$R$_{10}$R$_{14}$,
where each R$_{19}$ is independently H, alkyl, C$_2$-C$_{12}$ alkyl, alkenyl, C$_4$-C$_{12}$ alkenyl, alkynyl, aryl, substituted aryl where the substituent is other than chloro when $R_1$ and $R_2$ are =O, —CH$_2$CN, —CH$_2$CO$_2$R$_{11}$, —CH$_2$COR$_{11}$, —NHR$_{11}$ or —NH(R$_{11}$)$_2$,
wherein each R$_{11}$ is independently alkyl, alkenyl or alkynyl, or H;
$R_5$ and $R_6$ is each independently H, OH, or $R_5$ and $R_6$ taken together are =O;
$R_7$ and $R_8$ is each independently H, F, Cl, Br, SO$_2$Ph, CO$_2$CH$_3$, or SR$_{12}$,
where R$_{12}$ is H, alkyl, alkenyl, alkynyl or aryl; and
each occurrence of alkyl, alkenyl, or alkynyl is branched or unbranched, unsubstituted or substituted,
or a salt, enantiomer or zwitterion of the compound.

DETAILED DESCRIPTION OF THE INVENTION

A method of increasing the insulin sensitivity of a mammalian cell by contacting the cell with a protein phosphatase 2A (PP2A) inhibitor having the structure:

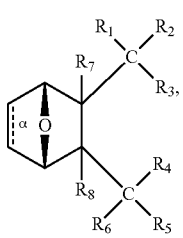

wherein
bond α is present or absent;
$R_1$ and $R_2$, is each independently H, $O^-$ or $OR_9$,
  where $R_9$ is H, alkyl, alkenyl, alkynyl or aryl,
  or $R_1$ and $R_2$ together are =O;
$R_3$ and $R_4$ are each different, and each is OH, $O^-$, $OR_9$, $OR_{10}$, $O(CH_2)_{1-6}R_9$, SH, $S^-$, $SR_9$,

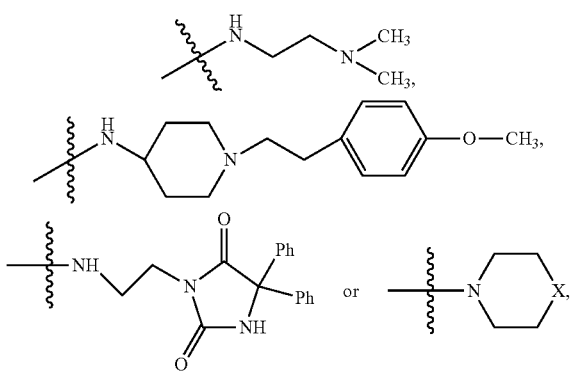

where X is O, S, $NR_{10}$, or $N^+R_{10}R_{10}$,
  where each $R_{10}$ is independently H, alkyl, $C_2$-$C_{12}$alkyl, alkenyl, $C_4$-$C_{12}$ alkenyl, alkynyl, aryl, substituted aryl where the substituent is other than chloro when $R_1$ and $R_2$ are =O,

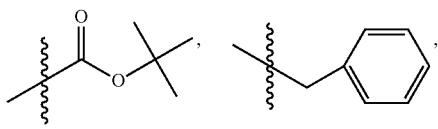

—$CH_2CN$, —$CH_2CO_2R_{11}$, —$CH_2COR_{11}$, —$NHR_{11}$ or —$NH(R_{11})_2$,
  wherein each $R_{11}$ is independently alkyl, alkenyl or alkynyl, or H;
$R_5$ and $R_6$ is each independently H, OH, or $R_5$ and $R_6$ taken together are =O;
$R_7$ and $R_8$ is each independently H, F, Cl, Br, $SO_2Ph$, $CO_2CH_3$, or $SR_{12}$,
  where $R_{12}$ is H, alkyl, alkenyl, alkynyl or aryl; and
each occurrence of alkyl, alkenyl, or alkynyl is branched or unbranched, unsubstituted or substituted,
or a salt, enantiomer or zwitterion of the compound.

In one embodiment, the method wherein glucose uptake into the mammalian cell is increased.

In one embodiment, the method wherein glucose concentration surrounding the mammalian cell is decreased.

In one embodiment, the method wherein dephosphorylation of Akt in the mammalian cell is reduced.

In one embodiment, the method wherein inactivation of Akt in the mammalian cell is reduced.

In one embodiment, the method wherein phosphorylation of Akt in the mammalian cell is increased.

In one embodiment, the method wherein activation of Akt in the mammalian cell is increased.

In one embodiment, the method wherein the increase in insulin sensitivity comprises increased phosphorylation of Akt in the mammalian cell.

In one embodiment, the method wherein the increase in insulin sensitivity comprises increased activation of Akt in the mammalian cell.

In one embodiment, the method wherein dephosphorylation of Akt by protein phosphatase 2A (PP2A) in the mammalian cell is reduced.

In one embodiment, the method wherein inactivation of Akt by protein phosphatase 2A (PP2A) in the mammalian cell is reduced.

In one embodiment, the method wherein the mammalian cell is a liver, fat, muscle or endothial cell.

In one embodiment, the method wherein the protein phosphatase 2A inhibitor inhibits protein phosphatase 2A activity in hepatocytes, muscle cells, retinal endothelial cells, endothelial cells of the microvasculature in general, including the feet, or pancreatic islet β-cells.

In one embodiment, the method wherein the protein phosphatase 2A inhibitor reduces dephosphorylation of Akt in hepatocytes, muscle cells, retinal endothelial cells, endothelial cells of the microvasculature in general, including the feet, or pancreatic islet β-cells.

In one embodiment, the method wherein the protein phosphatase 2A inhibitor reduces inactivation of Akt in hepatocytes, muscle cells, endothelial cells of the microvasculature in general, including the feet, retinal endothelial cells or pancreatic islet β-cells.

In one embodiment, the method wherein the protein phosphatase 2A inhibitor increases phosphorylation of Akt in hepatocytes, muscle cells, retinal endothelial cells, endothelial cells of the microvasculature in general, including the feet, or pancreatic islet β-cells.

In one embodiment, the method wherein the protein phosphatase 2A inhibitor increases activation of Akt in hepatocytes, muscle cells, endothelial cells of the microvasculature in general, including the feet, retinal endothelial cells or pancreatic islet β-cells.

A method of treating Type 2 Diabetes in a subject afflicted with Type 2 Diabetes comprising administering to the subject a therapeutically effective amount of a protein phosphatase 2A inhibitor having the structure:

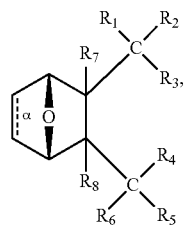

wherein
bond α is present or absent;
$R_1$ and $R_2$ is each independently H, $O^-$ or $OR_9$,
  where $R_9$ is H, alkyl, alkenyl, alkynyl or aryl,
  or $R_1$ and $R_2$ together are =O;

$R_3$ and $R_4$ are each different, and each is OH, O$^-$, OR$_9$, OR$_{10}$, O(CH$_2$)$_{1-6}$R$_9$, SH, S$^-$, SR$_9$,

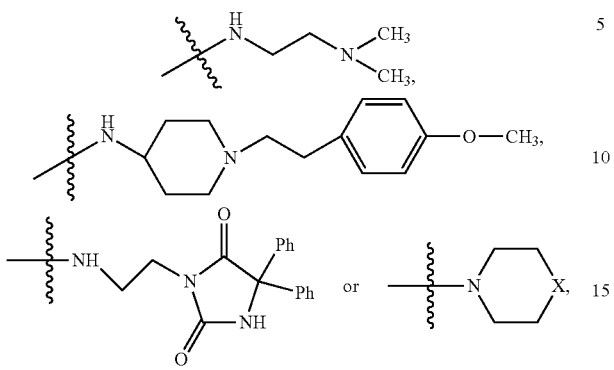

where X is O, S, NR$_{10}$, or N$^+$R$_{10}$R$_{10}$,
where each R$_{10}$ is independently H, alkyl, C$_2$-C$_{12}$ alkyl, alkenyl, C$_4$-C$_{12}$ alkenyl, alkynyl, aryl, substituted aryl where the substituent is other than chloro when R$_1$ and R$_2$ are =O,

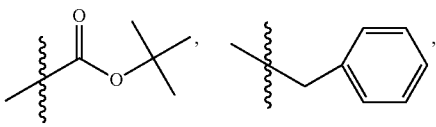

—CH$_2$CN, —CH$_2$CO$_2$R$_{11}$, —CH$_2$COR$_{11}$, —NHR$_{11}$ or —NH(R$_{11}$)$_2$,
wherein each R$_{11}$ is independently alkyl, alkenyl or alkynyl, or H;
R$_5$ and R$_6$ is each independently H, OH, or R$_5$ and R$_6$ taken together are =O;
R$_7$ and R$_8$ is each independently H, F, Cl, Br, SO$_2$Ph, CO$_2$CH$_3$, or SR$_{12}$,
where R$_{12}$ is H, alkyl, alkenyl, alkynyl or aryl; and
each occurrence of alkyl, alkenyl, or alkynyl is branched or unbranched, unsubstituted or substituted,
or a salt, enantiomer or zwitterion of the compound.

In one embodiment, the method wherein the protein phosphatase 2A increases insulin sensitivity in the subject afflicted with Type 2 Diabetes.

In one embodiment, the method wherein the protein phosphatase 2A inhibitor reduces insulin resistance in the subject afflicted with Type 2 Diabetes.

In one embodiment, the method wherein the protein phosphatase 2A inhibitor reduces Type 2 Diabetes related vascular injury in the liver, muscle, retina and pancreas.

In one embodiment, the method wherein the protein phosphatase 2A inhibitor reduces Type 2 Diabtetes related vascular injury caused by disruption of the endothielial barrier.

In one embodiment, the method wherein the protein phosphatase 2A inhibitor inhibits protein phosphatase 2A activity in hepatocytes, muscle cells, retinal endothelial cells, endothelial cells of the microvasculature, or pancreatic islet β-cells of the subject afflicted with Type 2 Diabetes.

In one embodiment, the method wherein the protein phosphatase 2A inhibitor reduces dephosphorylation of Akt in hepatocytes, muscle cells, retinal endothelial cells, endothelial cells of the microvasculature, or pancreatic islet β-cells of the subject afflicted with Type 2 Diabetes.

In one embodiment, the method wherein the protein phosphatase 2A inhibitor prevents inactivation of Akt in hepatocytes, muscle cells, retinal endothelial cells, endothelial cells of the microvasculature or pancreatic islet β-cells of the subject afflicted with Type 2 Diabetes.

A method of reducing complications associated with Type 2 Diabetes in a subject afflicted with Type 2 Diabetes comprising administering to the subject a therapeutically effective amount of a protein phosphatase 2A inhibitor having the structure:

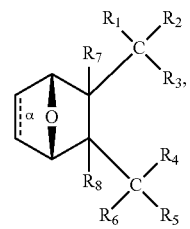

wherein
bond α is present or absent;
R$_1$ and R$_2$ is each independently H, O$^-$ or OR$_9$,
where R$_9$ is H, alkyl, alkenyl, alkynyl or aryl,
or R$_1$ and R$_2$ together are =O;
R$_3$ and R$_4$ are each different, and each is OH, O$^-$, OR$_9$, OR$_{10}$, O(CH$_2$)$_{1-6}$R$_9$, SH, S$^-$, SR$_9$,

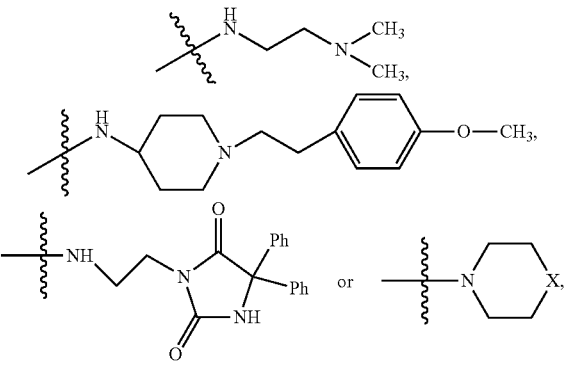

where X is O, S, NR$_{10}$, or N$^+$R$_{10}$R$_{10}$,
where each R$_{10}$ is independently H, alkyl, C$_2$-C$_{12}$ alkyl, alkenyl, C$_4$-C$_{12}$ alkenyl, alkynyl, aryl, substituted aryl where the substituent is other than chloro when R$_1$ and R$_2$ are =O,

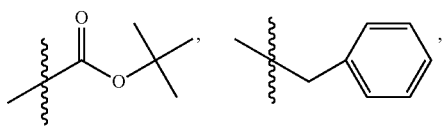

—CH$_2$CN, —CH$_2$CO$_2$R$_{11}$, —CH$_2$COR$_{11}$, —NHR$_{11}$ or —NH(R$_{11}$)$_2$,
wherein each R$_{11}$ is independently alkyl, alkenyl or alkynyl, or H;
R$_5$ and R$_6$ is each independently H, OH, or R$_5$ and R$_6$ taken together are =O;

$R_7$ and $R_8$ is each independently H, F, Cl, Br, $SO_2Ph$, $CO_2CH_3$, or $SR_{12}$,
  where $R_{12}$ is H, alkyl, alkenyl, alkynyl or aryl; and
each occurrence of alkyl, alkenyl, or alkynyl is branched or unbranched, unsubstituted or substituted,
or a salt, enantiomer or zwitterion of the compound.

In one embodiment, the protein phosphatase 2A inhibitor has the structure

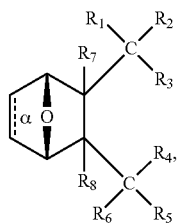

wherein
bond α is present or absent;
$R_1$ and $R_2$ is each independently H, O⁻ or $OR_9$,
  where $R_9$ is H, alkyl, alkenyl, alkynyl or aryl,
  or $R_1$ and $R_2$ together are =O;
$R_3$ and $R_4$ are each different, and each is OH, O⁻, $OR_9$, SH, S⁻, $SR_9$,

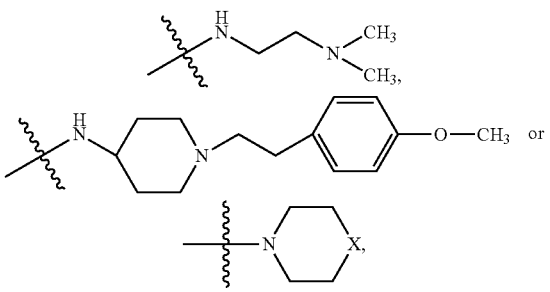

where X is O, S, $NR_{10}$, or $N^+R_{10}R_{13}$,
  where each $R_{10}$ is independently H, alkyl, $C_2$-$C_{12}$ alkyl, alkenyl, $C_4$-$C_{12}$ alkenyl, alkynyl, aryl, substituted aryl where the substituent is other than chloro when $R_1$ and $R_2$ are =O,

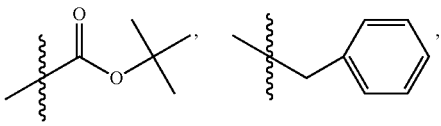

—$CH_2CN$, —$CH_2CO_2R_{11}$, —$CH_2COR_{11}$, —$NHR_{11}$ or —$NH^+(R_{11})_2$,
  where each $R_{11}$ is independently alkyl, alkenyl, alkynyl, or H;
$R_5$ and $R_6$ is each independently H, OH, or $R_5$ and $R_6$ taken together are =O; and
$R_7$ and $R_8$ is each independently H, F, Cl, Br, $SO_2Ph$, $CO_2CH_3$, or $SR_{12}$, where $R_{12}$ is H, aryl, alkyl, alkenyl or alkynyl,
or a salt, enantiomer or zwitterion of the compound.

In one embodiment, the protein phosphatase 2A inhibitor has the structure

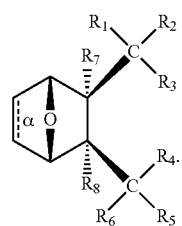

In one embodiment, the protein phosphatase 2A inhibitor has the structure

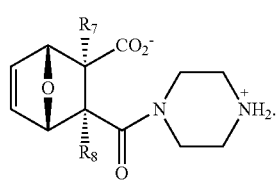

In one embodiment, the protein phosphatase 2A inhibitor has the structure

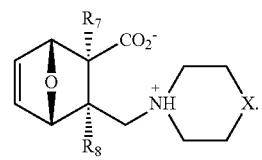

In one embodiment, bond α is present. In another embodiment, bond α is absent.

In one embodiment, $R_1$ and $R_2$ together are =O;
$R_3$ is O⁻ or $OR_9$, where $R_9$ is H, methyl, ethyl or phenyl;
$R_4$ is

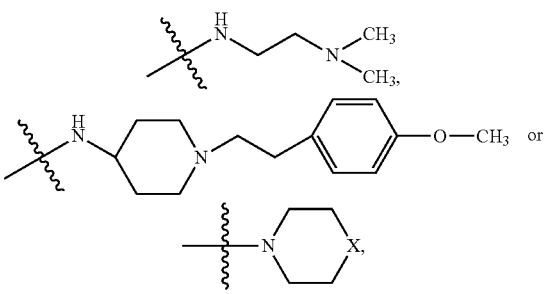

where X is O, S, $NR_{10}$, or $N^+R_{10}R_{10}$,
  where each $R_{10}$ is independently H, alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro,

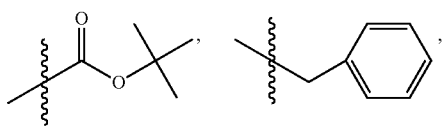

—$CH_2CN$, —$CH_2CO_2R_{11}$, —$CH_2COR_{11}$, —$NHR_{11}$ or —$NH^+(R_{11})_2$, where $R_{11}$ is alkyl, alkenyl or alkynyl, each of which is substituted or unsubstituted, or H;

$R_5$ and $R_6$ taken together are =O; and $R_7$ and $R_8$ is each independently H, F, Cl, Br, $SO_2Ph$, $CO_2CH_3$, or $SR_{12}$, where $R_{12}$ is a substituted or unsubstituted alkyl, alkenyl or alkynyl.

In one embodiment, $R_3$ is $O^-$.

In another embodiment, $R_4$ is

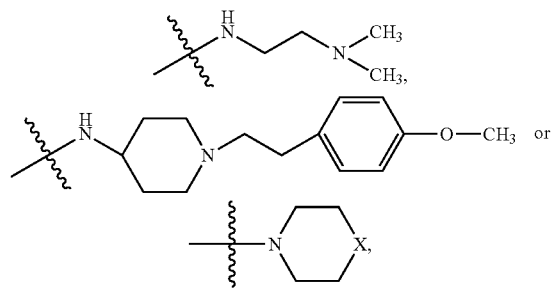

where X is O, $NR_{10}$, $N^+R_{10}R_{10}$ where each $R_{10}$ is independently H, alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro when $R_1$ and $R_2$ are =O,

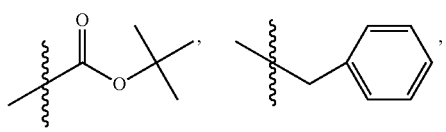

—$CH_2CN$, —$CH_2CO_2R_{11}$, —$CH_2COR_{11}$, —$NHR_{11}$ or —$NH^+(R_{11})_2$, where $R_{11}$ is H or alkyl.

In one embodiment, the protein phosphatase inhibitor 2A has the structure

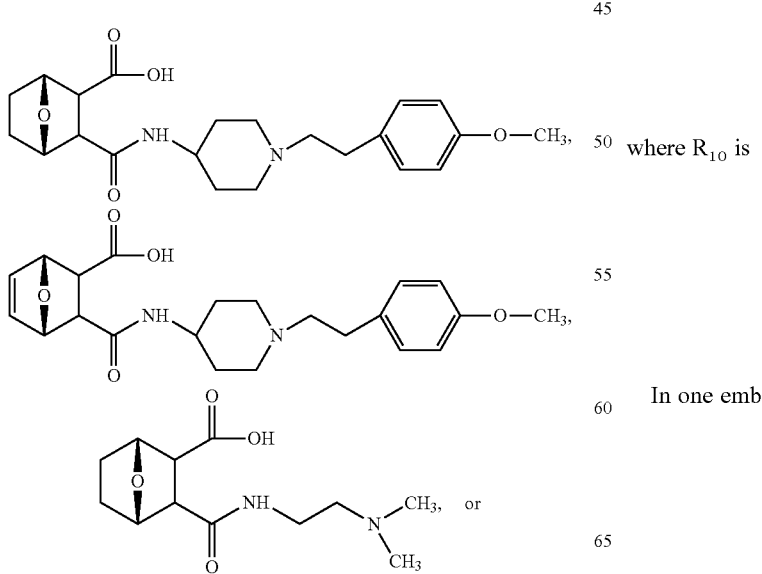

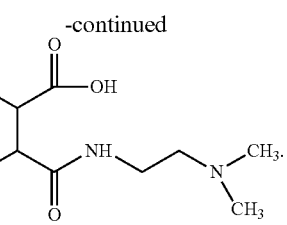

In one embodiment, $R_4$ is

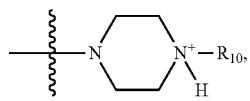

where $R_{10}$ is H, alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro, when $R_1$ is $R_1$ are =O,

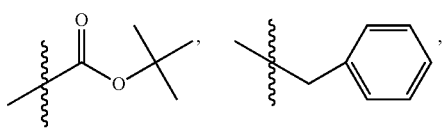

—$CH_2CN$, —$CH_2CO_2R_{11}$, —$CH_2COR_{11}$, —$NHR_{11}$ or —$NH^+(R_{11})_2$, where $R_{11}$ is H or alkyl.

In one embodiment, $R_4$ is

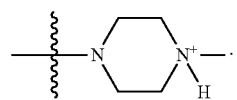

In one embodiment, $R_4$ is

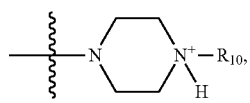

where $R_{10}$ is

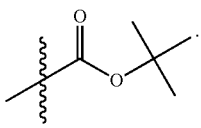 [SMILES: *C(=O)OC(C)(C)C]

In one embodiment, $R_4$ is

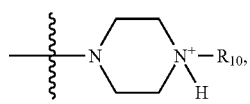

where $R^{10}$ is

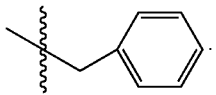 [SMILES: *Cc1ccccc1]

In one embodiment, $R_4$ is

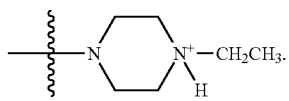

In one embodiment, $R_4$ is

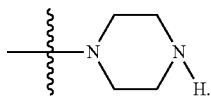

In one embodiment, $R_5$ and $R_6$ together are =O. In another embodiment, $R_7$ and $R_8$ are each H.

In one embodiment,

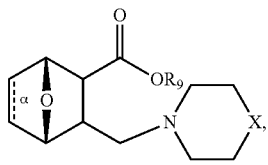

wherein bond α is present or absent;
$R_9$ is present or absent and when present is H, $C_1$-$C_{10}$ alkyl, $C_2$-$C_{10}$ alkenyl or phenyl; and X is O, S, $NR_{10}$ or $N^+R_{10}R_{10}$,
where each $R_{10}$ is independently H, alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro,

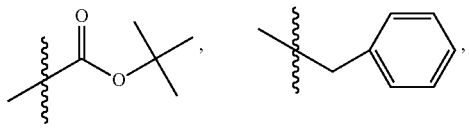

—$CH_2CO_2R_{11}$, —$CH_2COR_{11}$, —$CH_2CN$, or —$CH_2CH_2R_{16}$, where $R_{11}$ is H or alkyl, and where $R_{15}$ is any substitutent that is a precursor to an aziridinyl intermediate,
or a salt, zwitterion or enantiomer of the compound.

In one embodiment, the protein phosphatase 2A inhibitor has the structure

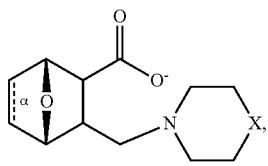

wherein,
bond α is present or absent;
X is O, S, $NR_{10}$ or $N^+R_{10}R_{10}$,
where each $R_{10}$ is independently H, alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro,

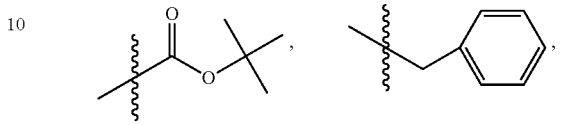

—$CH_2CO_2R_{11}$, —$CH_2COR_{11}$, —$CH_2CN$, or —$CH_2CH_2R_{16}$, where $R_{11}$ is H or alkyl, and where $R_{16}$ is any substitutent that is a aziridinyl intermediate,
or a salt, zwitterion or enantiomer of a compound.

In one embodiment,
X is O or $NH^+R_{10}$,
where $R_{10}$ is H, alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro,

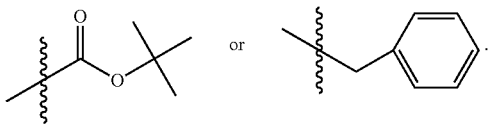

In one embodiment, X is —$CH_2CH_2R_{16}$, where $R_{16}$ is any substitutent that is a precursor to an aziridinyl intermediate.

In one embodiment, X is O.

In another embodiment, X is $NH^+R_{10}$,
where $R^{10}$ H, alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro,

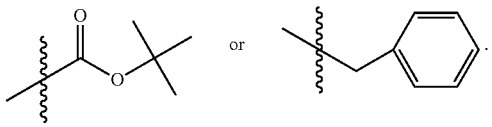

In one embodiment, $R_{10}$ is methyl. In another embodiment, $R_{10}$ is

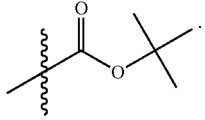 [SMILES: *C(=O)OC(C)(C)C]

In one embodiment, $R^{10}$ is

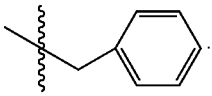

In one embodiment, $R_{10}$ is ethyl. In another embodiment, $R_{10}$ is absent.

In one embodiment, the protein phosphatase 2A inhibitor has the structure

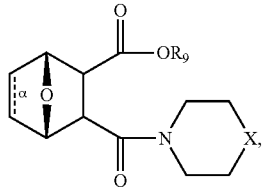

wherein
bond α is present or absent;
$R_9$ is present or absent and when present is H, alkyl, alkenyl, alkynyl or phenyl; and
X is O, $NR_{10}$, or $N^+R_{10}R_{10}$,
  where each $R_{10}$ is indepdently H, alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro,

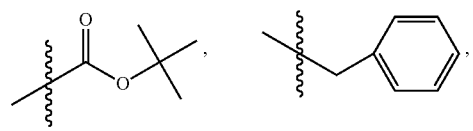

—$CH_2CN$, —$CH_2CO_2R_{12}$, or —$CH_2COR_{12}$
  where $R_{12}$ is H or alkyl,
or a salt, zwitterion, or enantiomer of the compound.

In one embodiment, the protein phosphatase 2A inhibitor has the structure

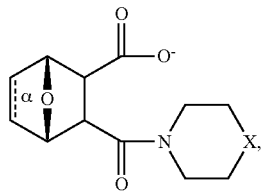

wherein
bond α is present or absent;
X is O or $NH^+R_{10}$,
  where $R_{10}$ is H, alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro,

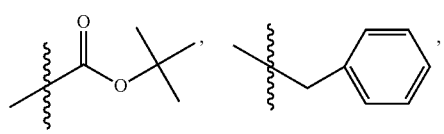

—$CH_2CN$, —$CH_2CO_2R_2$, or —$CH_2COR_{12}$, where $R_{12}$ is H or alkyl.

In one embodiment, bond α is present. In another embodiment, bond α is absent.

In one embodiment, the protein phosphatase 2A inhibitor has the structure

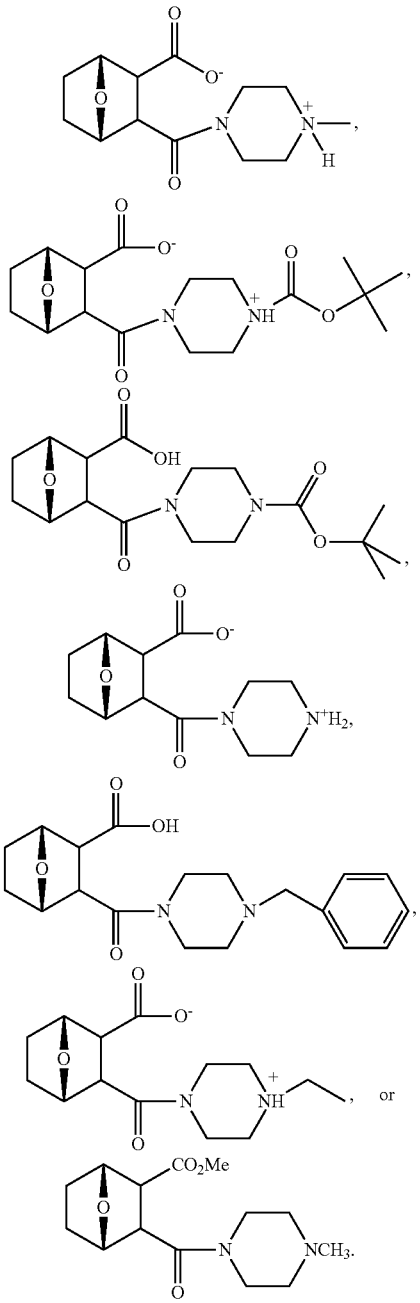

In one embodiment, the protein phosphatase 2A inhibitor has the structure

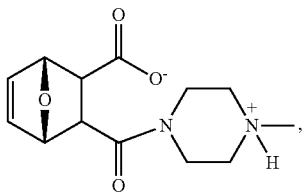

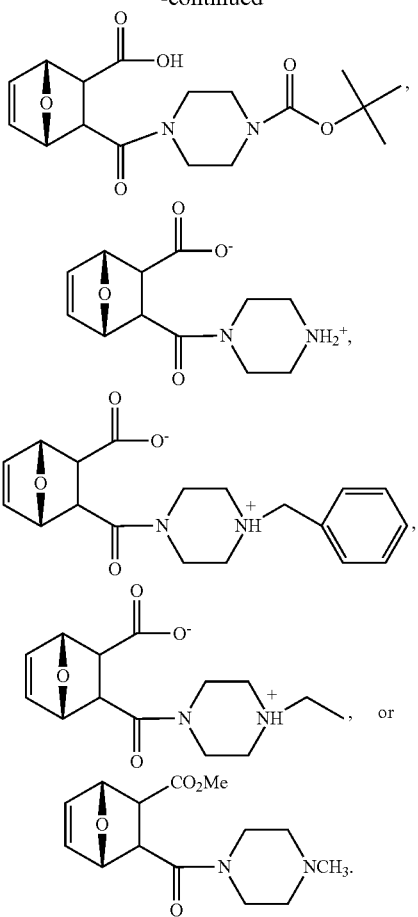

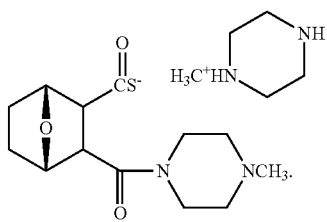

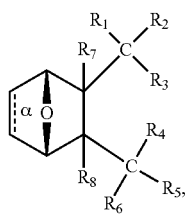

In one embodiment, the protein phosphatase 2A inhibitor has the structure

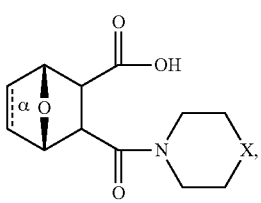

wherein
bond α is present or absent;
X is $NH^+R_{10}$,
  where $R_{10}$ is present or absent and when present $R_{10}$ is alkyl, substituted $C_2$-$C_{12}$ alkyl, alkenyl, substituted $C_4$-$C_{12}$ alkenyl,

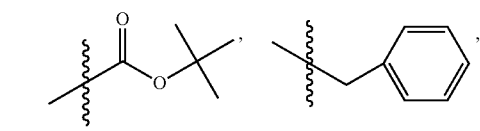

—$CH_2CN$, —$CH_2CO_2R_{12}$, or —$CH_2COR_{12}$, where $R_{12}$ is H or alkyl.

In one embodiment of the method, the protein phosphatase 2A inhibitor has the structure In one embodiment of the method, the protein phosphatase 2A inhibitor has the structure

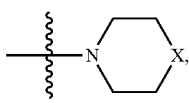

wherein
bond α is present or absent;
$R_1$ and $R_2$ is each independently H, $O^-$ or $OR_9$,
  where $R_9$ is H, alkyl, substituted alkyl, alkenyl, alkynyl or aryl,
or $R_1$ and $R_2$ together are =O;
$R_3$ and $R_4$ are each different, and each is $O(CH_2)_{1-6}R_9$ or $OR_9$,
or

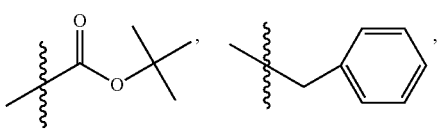

where X is O, S, $NR_{10}$, or $N^+R_{10}R_{10}$,
  where each $R_{10}$ is independently H, alkyl, hydroxyalkyl, $C_2$-$C_2$ alkyl, alkenyl, $C_4$-$C_{12}$ alkenyl, alkynyl, aryl, substituted aryl where the substituent is other than chloro when $R_1$ and $R_2$ are =O,

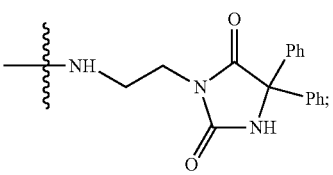 [SMILES: *NCCN1C(=O)NC(c2ccccc2)(c2ccccc2)C1=O]

—$CH_2CN$, —$CH_2CO_2R_{11}$, —$CH_2COR_{11}$, —$NHR_{11}$ or —$NH^+(R_{11})_2$,
  where each $R_{11}$ is independently alkyl, alkenyl or alkynyl, each of which is substituted or unsubstituted, or H;
or $R_3$ and $R_4$ are each different and each is OH or $R_5$ and $R_6$ is each independently H, OH, or $R_5$ and $R_6$ taken together are =O;

$R_7$ and $R_8$ is each independently H, F, Cl, Br, $SO_2Ph$, $CO_2CH_3$, or $SR_{12}$, where $R_{12}$ is H, aryl or a substituted or unsubstituted alkyl, alkenyl or alkynyl; and each occurrence of alkyl, alkenyl, or alkynyl is branched or unbranched, unsubstituted or substituted, or a salt, enantiomer or zwitterion of the compound.

In one embodiment of the method, the protein phosphatase 2A inhibitor has the structure

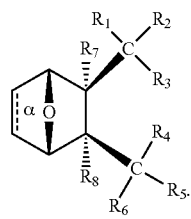

In one embodiment of the method, the bond α is present.

In one embodiment of the method, the bond α is absent.

In one embodiment of the method, $R_3$ is $OR_9$ or $O(CH_2)_{1-6}R_9$, where $R_9$ is aryl, substituted ethyl or substituted phenyl, wherein the substituent is in the para position of the phenyl;

$R_4$ is

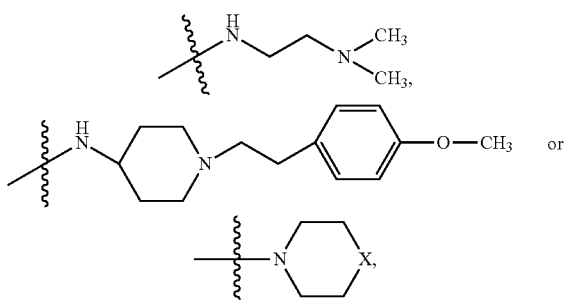

where X is O, S, $NR_{10}$, or $N^+R_{10}R_{10}$, where each $R_{10}$ is independently H, alkyl, hydroxyalkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro,

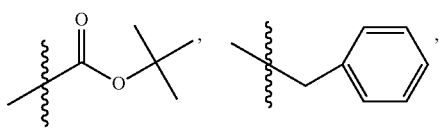

—$CH_2CN$, —$CH_2CO_2R_{11}$, —$CH_2COR_{11}$, —$NHR_{11}$ or —$NH(R_{11})_2$, where $R_{11}$ is alkyl, alkenyl or alkynyl, each of which is substituted or unsubstituted, or H;

or where $R_3$ is OH and $R_4$ is

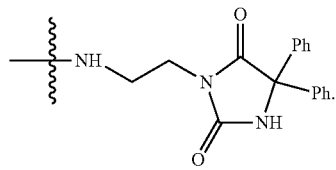 [SMILES: *NCCN1C(=O)NC(c2ccccc2)(c2ccccc2)C1=O]

In one embodiment of the method, $R_4$ is

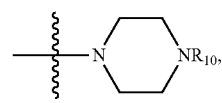

where $R^{10}$ is alkyl or hydroxylalkyl or $R_4$ is

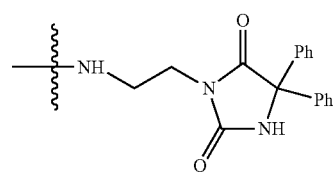 [SMILES: *NCCN1C(=O)NC(c2ccccc2)(c2ccccc2)C1=O]

when $R_3$ is OH.

In one embodiment of the method, $R_1$ and $R_2$ together are =O;

$R_3$ is $OR_9$ or $O(CH_2)_{1-2}R_9$, where $R_9$ is aryl, substituted ethyl, or substituted phenyl, wherein the substituent is in the para position of the phenyl;

or $R_3$ is OH and $R_4$ is

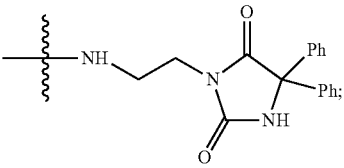 [SMILES: *NCCN1C(=O)NC(c2ccccc2)(c2ccccc2)C1=O]

$R_4$ is

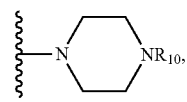

where $R_{10}$ is alkyl or hydroxyl alkyl;

$R_5$ and $R_6$ together are =O; and $R_7$ and $R_8$ are each independently H.

In one embodiment of the method, $R_1$ and $R_2$ together are =O;

$R_3$ is OH, $O(CH_2)R_9$, or $OR_9$, where $R_9$ is phenyl or $CH_2CCl_3$,

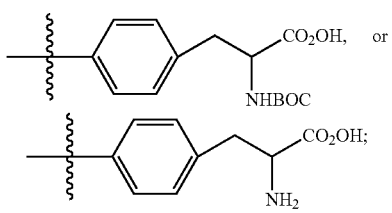

$R_4$ is

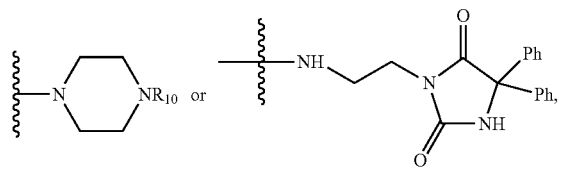

where $R_{10}$ is $CH_3$ or $CH_3CH_2OH$;
$R_5$ and $R_6$ together are =O; and
$R_7$ and $R_8$ are each independently H.
In one embodiment of the method,
$R_3$ is $OR_9$
   where $R_9$ is $(CH_2)_{1-6}(CHNHBOC)CO_2H$, $(CH_2)_{1-6}(CHNH_2)CO_2H$, or $(CH_2)_{1-6}CCl_3$.
In one embodiment of the method,
$R_9$ is $CH_2(CHNHBOC)CO_2H$, $CH_2(CHNH_2)CO_2H$, or $CH_2CCl_3$.
In one embodiment of the method,
$R_3$ is $O(CH_2)_{1-6}R_9$ or $O(CH_2)R_9$,
   where $R_9$ is phenyl.
In one embodiment of the method,
$R_3$ is $O(CH_2)R_9$
   where $R_9$ is phenyl.
In one embodiment of the method,
$R_3$ is OH and $R_4$ is

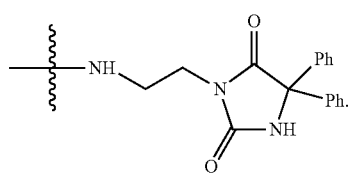 [SMILES: *NCCN1C(=O)NC(c2ccccc2)(c2ccccc2)C1=O]

In one embodiment of the method,
$R_4$ is

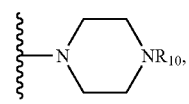

wherein $R_{10}$ is alkyl or hydroxyalkyl.
In one embodiment of the method, $R_{11}$ is —$CH_2CH_2OH$ or —$CH_3$.
In one embodiment of the method, the protein phosphatase 2A inhibitor has the structure

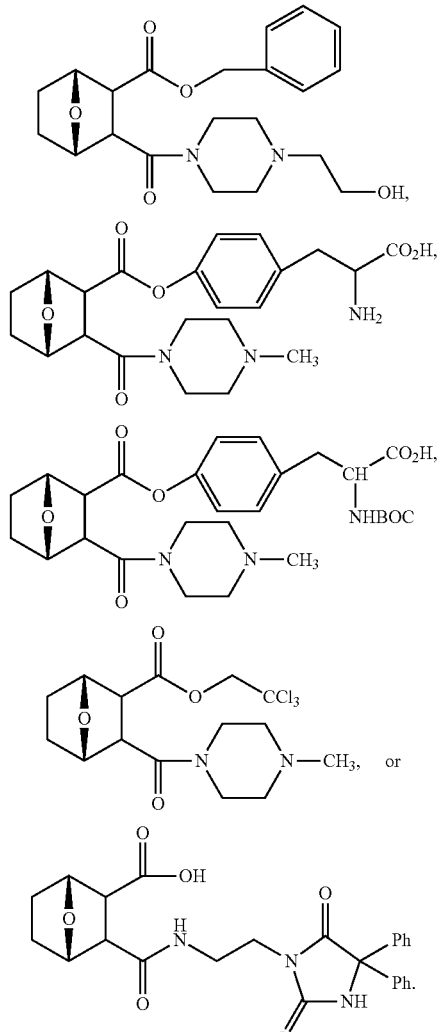

In one embodiment of the method, the protein phosphatase 2A inhibitor has the structure

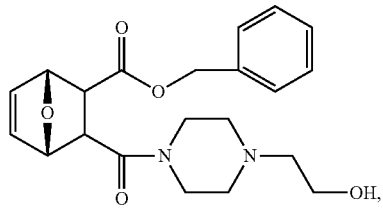

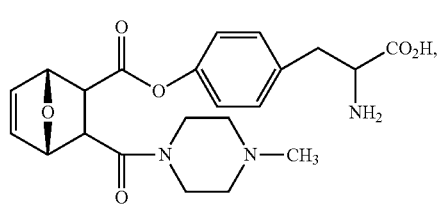

-continued

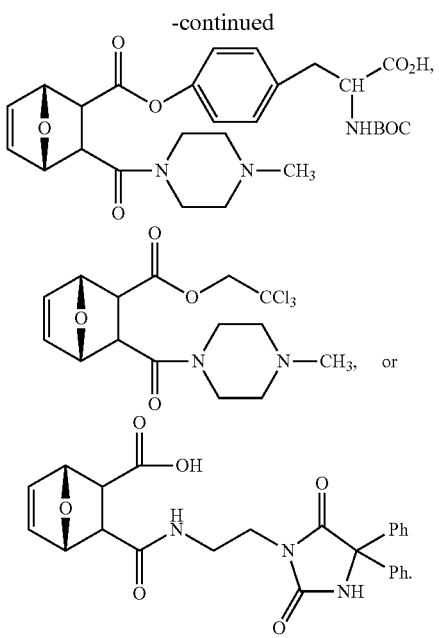

For the foregoing embodiments, each embodiment disclosed herein is contemplated as being applicable to each of the other disclosed embodiments. Thus, all combinations of the various elements described herein are within the scope of the invention.

Definitions

As used herein, and unless otherwise stated, each of the following terms shall have the definition set forth below.

In particular, the invention is directed to the treatment of Type 2 Diabetes.

As used herein, "Type 2 Diabetes" is a disease consisting of an array of dysfunctions including, but not limited to, high blood glucose levels, insulin resistance, inadequate insulin secretion, and excessive or inappropriate glucagon secretion. Type 2 diabetes is associated with an array of complications, including microvascular, macrovascular, and neuropathic complications. Microvascular complications of diabetes include retinal, renal, and possibly neuropathic disease. Macrovascular complications include coronary artery and peripheral vascular disease. Diabetic neuropathy affects autonomic and peripheral nerves. Type 2 Diabetes is also associated with atherosclerosis, low glucose tolerance, dyslipidemia, hyperlipidemia, hypertriglyceridemia, and hypercholesterolemia.

As used herein, "Insulin Resistance" is a physiological condition where the natural hormone insulin becomes less effective at lowering blood sugar levels.

As used herein, "Insulin Sensitivity" is a measure of the tissue response to insulin and refers to insulin's ability to cause tissues to absorb glucose from the blood. A loss of insulin sensitivity may also be called insulin resistance.

As used herein, a "symptom" associated with Type 2 Diabetes includes any clinical or laboratory manifestation associated with Type 2 Diabetes and is not limited to what the subject can feel or observe.

As used herein, "treatment of the diseases" or "treating", e.g. of Type 2 Diabetes, encompasses inducing inhibition, regression, or stasis of the disease or a symptom or condition associated with the disease.

As used herein, "inhibition" of disease encompasses preventing or reducing the disease progression and/or disease complication in the subject.

As used herein, "alkyl" is intended to include both branched and straight-chain saturated aliphatic hydrocarbon groups having the specified number of carbon atoms. Thus, $C_1$-$C_n$ as in "$C_1$-$C_n$ alkyl" is defined to include groups having 1, 2, . . . , n–1 or n carbons in a linear or branched arrangement, and specifically includes methyl, ethyl, propyl, butyl, pentyl, hexyl, and so on. An embodiment can be $C_1$-$C_{12}$ alkyl. "Alkoxy" represents an alkyl group as described above attached through an oxygen bridge.

The term "alkenyl" refers to a non-aromatic hydrocarbon radical, straight or branched, containing at least 1 carbon to carbon double bond, and up to the maximum possible number of non-aromatic carbon-carbon double bonds may be present. Thus, $C_2$-$C_n$ alkenyl is defined to include groups having 1, 2 . . . , n–1 or n carbons. For example, "$C_2$-$C_6$ alkenyl" means an alkenyl radical having 2, 3, 4, 5, or 6 carbon atoms, and at least 1 carbon-carbon double bond, and up to, for example, 3 carbon-carbon double bonds in the case of a $C_6$ alkenyl, respectively. Alkenyl groups include ethenyl, propenyl, butenyl and cyclohexenyl. As described above with respect to alkyl, the straight, branched or cyclic portion of the alkenyl group may contain double bonds and may be substituted if a substituted alkenyl group is indicated. An embodiment can be $C_2$-$C_{12}$ alkenyl.

The term "alkynyl" refers to a hydrocarbon radical straight or branched, containing at least 1 carbon to carbon triple bond, and up to the maximum possible number of non-aromatic carbon-carbon triple bonds may be present. Thus, $C_2$-$C_n$ alkynyl is defined to include groups having 1, 2 . . . , n–1 or n carbons. For example, "$C_2$-$C_6$ alkynyl" means an alkynyl radical having 2 or 3 carbon atoms, and 1 carbon-carbon triple bond, or having 4 or 5 carbon atoms, and up to 2 carbon-carbon triple bonds, or having 6 carbon atoms, and up to 3 carbon-carbon triple bonds. Alkynyl groups include ethynyl, propynyl and butynyl. As described above with respect to alkyl, the straight or branched portion of the alkynyl group may contain triple bonds and may be substituted if a substituted alkynyl group is indicated. An embodiment can be a $C_2$-$C_n$ alkynyl.

As used herein, "aryl" is intended to mean any stable monocyclic or bicyclic carbon ring of up to 10 atoms in each ring, wherein at least one ring is aromatic. Examples of such aryl elements include phenyl, naphthyl, tetrahydro-naphthyl, indanyl, biphenyl, phenanthryl, anthryl or acenaphthyl. In cases where the aryl substituent is bicyclic and one ring is non-aromatic, it is understood that attachment is via the aromatic ring. The substituted aryls included in this invention include substitution at any suitable position with amines, substituted amines, alkylamines, hydroxys and alkylhydroxys, wherein the "alkyl" portion of the alkylamines and alkylhydroxys is a $C_2$-$C_n$ alkyl as defined hereinabove. The substituted amines may be substituted with alkyl, alkenyl, alkynl, or aryl groups as hereinabove defined.

The alkyl, alkenyl, alkynyl, and aryl substituents may be unsubstituted or unsubstituted, unless specifically defined otherwise. For example, a ($C_1$-$C_6$) alkyl may be substituted with one or more substituents selected from OH, oxo, halogen, alkoxy, dialkylamino, or heterocyclyl, such as morpholinyl, piperidinyl, and so on.

In the compounds of the present invention, alkyl, alkenyl, and alkynyl groups can be further substituted by replacing one or more hydrogen atoms by non-hydrogen groups described herein to the extent possible. These include, but are not limited to, halo, hydroxy, mercapto, amino, carboxy, cyano and carbamoyl.

The term "substituted" as used herein means that a given structure has a substituent which can be an alkyl, alkenyl, or aryl group as defined above. The term shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

As used herein, a "compound" is a small molecule that does not include proteins, peptides or amino acids.

As used herein, an "isolated" compound is a compound isolated from a crude reaction mixture or from a natural source following an affirmative act of isolation. The act of isolation necessarily involves separating the compound from the other components of the mixture or natural source, with some impurities, unknown side products and residual amounts of the other components permitted to remain. Purification is an example of an affirmative act of isolation.

As used herein, "administering" an agent may be performed using any of the various methods or delivery systems well known to those skilled in the art. The administering can be performed, for example, orally, parenterally, intraperitoneally, intravenously, intraarterially, transdermally, sublingually, intramuscularly, rectally, transbuccally, intranasally, liposomally, via inhalation, vaginally, intraoccularly, via local delivery, subcutaneously, intraadiposally, intraarticularly, intrathecally, into a cerebral ventricle, intraventicularly, intratumorally, into cerebral parenchyma or intraparenchchymally.

The following delivery systems, which employ a number of routinely used pharmaceutical carriers, may be used but are only representative of the many possible systems envisioned for administering compositions in accordance with the invention.

Injectable drug delivery systems include solutions, suspensions, gels, microspheres and polymeric injectables, and can comprise excipients such as solubility-altering agents (e.g., ethanol, propylene glycol and sucrose) and polymers (e.g., polycaprylactones and PLGA's).

Other injectable drug delivery systems include solutions, suspensions, gels. Oral delivery systems include tablets and capsules. These can contain excipients such as binders (e.g., hydroxypropylmethylcellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc).

Implantable systems include rods and discs, and can contain excipients such as PLGA and polycaprylactone.

Oral delivery systems include tablets and capsules. These can contain excipients such as binders (e.g., hydroxypropylmethylcellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc).

Transmucosal delivery systems include patches, tablets, suppositories, pessaries, gels and creams, and can contain excipients such as solubilizers and enhancers (e.g., propylene glycol, bile salts and amino acids), and other vehicles (e.g., polyethylene glycol, fatty acid esters and derivatives, and hydrophilic polymers such as hydroxypropylmethylcellulose and hyaluronic acid).

Dermal delivery systems include, for example, aqueous and nonaqueous gels, creams, multiple emulsions, microemulsions, liposomes, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer.

Solutions, suspensions and powders for reconstitutable delivery systems include vehicles such as suspending agents (e.g., gums, zanthans, cellulosics and sugars), humectants (e.g., sorbitol), solubilizers (e.g., ethanol, water, PEG and propylene glycol), surfactants (e.g., sodium lauryl sulfate, Spans, Tweens, and cetyl pyridine), preservatives and antioxidants (e.g., parabens, vitamins E and C, and ascorbic acid), anti-caking agents, coating agents, and chelating agents (e.g., EDTA).

As used herein, "pharmaceutically acceptable carrier" refers to a carrier or excipient that is suitable for use with humans and/or animals without undue adverse side effects (such as toxicity, irritation, and allergic response) commensurate with a reasonable benefit/risk ratio. It can be a pharmaceutically acceptable solvent, suspending agent or vehicle, for delivering the instant compounds to the subject.

The compounds used in the method of the present invention may be in a salt form. As used herein, a "salt" is a salt of the instant compounds which has been modified by making acid or base salts of the compounds. In the case of compounds used to treat an infection or disease, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", J. Pharm. Sci. 66:1-19).

As used herein, an "amount" or "dose" of an agent measured in milligrams refers to the milligrams of agent present in a drug product, regardless of the form of the drug product.

As used herein, the term "therapeutically effective amount" or "effective amount" refers to the quantity of a component that is sufficient to yield a desired therapeutic response without undue adverse side effects (such as toxicity, irritation, or allergic response) commensurate with a reasonable benefit/risk ratio when used in the manner of this invention. The specific effective amount will vary with such factors as the particular condition being treated, the physical condition of the patient, the type of mammal being treated, the duration of the treatment, the nature of concurrent therapy (if any), and the specific formulations employed and the structure of the compounds or its derivatives.

Where a range is given in the specification it is understood that the range includes all integers and 0.1 units within that range, and any sub-range thereof. For example, a range of 77 to 90% is a disclosure of 77, 78, 79, 80, and 81% etc.

As used herein, "about" with regard to a stated number encompasses a range of +one percent to −one percent of the stated value. By way of example, about 100 mg/kg therefore includes 99, 99.1, 99.2, 99.3, 99.4, 99.5, 99.6, 99.7, 99.8, 99.9, 100, 100.1, 100.2, 100.3, 100.4, 100.5, 100.6, 100.7, 100.8, 100.9 and 101 mg/kg. Accordingly, about 100 mg/kg includes, in an embodiment, 100 mg/kg. It is understood that where a parameter range is provided, all integers within that range, and tenths thereof, are also provided by the invention. For example, "0.2-5 mg/kg/day" is a disclosure of 0.2 mg/kg/day, 0.3 mg/kg/day, 0.4 mg/kg/day, 0.5 mg/kg/day, 0.6 mg/kg/day etc. up to 5.0 mg/kg/day.

All combinations of the various elements described herein are within the scope of the invention.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Example 1

Synthesis of LB-107

LB-107 (5) was prepared by reacting acid 3 with N-methylpiperizine (4) in the presence of EDC. In order to prepare 5 in better yields three different methods were attempted. In the first method, one pot reaction on LB-100 using thionyl chloride in methanol was attempted but no product was observed. In the second method, acid chloride of LB-100 was allowed to react with methanol in presence of triethylamine/DMAP to give the desired methyl ester. The methyl ester thus obtained was in low yields and the separation of triethylamine from the product was also tedious. Hence a two-step procedure was used. In this third method, endothal (1) when heated under reflux in methanol gave the desired monomethylester 3 in 95% yields. Compound 3 when treated with N-methylpiperazine (4) in presence of EDC and a catalytic amount of N-hydroxybenzotriazole gave the required methyl ester 5 in 39% yields after purification with column chromatography.

7-Oxa-bicyclo [2,2,1]heptane-2,3-dicarboxylic acid monomethyl ester (3)

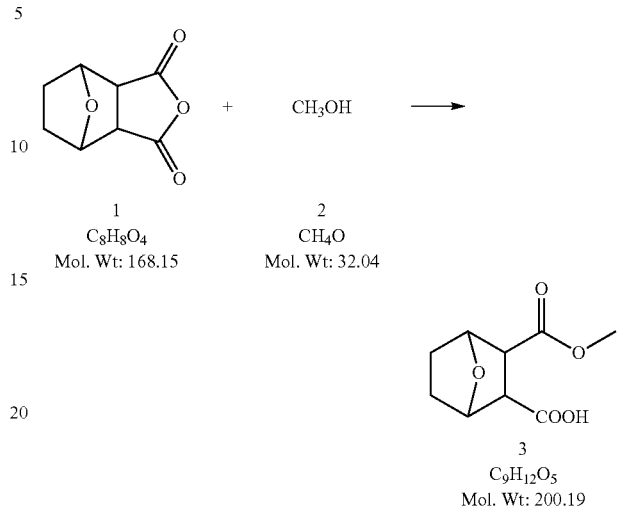

The mixture of exo-7-Oxabicyclo[2.2.1]heptane-2,3-dicarboxylic anhydride (1, 10.0 g, 59.5 mmole) and dry methanol (2, 50 mL) was heated at reflux temperature for 3.5 h. The reaction mixture became homogeneous during the reflux. The reaction mixture was then cooled down to room temperature and concentrated to give 3 (11.3 g, 95%) as crystalline white material. The crude $^1$H NMR was clean enough with no extra peaks. Hence this material was utilized in the next step without further purification. $^1$H NMR (DMSO-$d_6$) δ 1.52 (m, 4H), 2.98 (s, 2H), 3.49 (s, 3H), 4.66 (d, 2H), 12.17 (s, 1H).

3-(4-Methylpiperazine-1-carbonyl)-7-oxa-bicyclo[2,2,1]heptane-2-carboxylic acid methyl ester (5)

To a mixture of acid 3 (2.00 g, 10.0 mmole) in 50 mL of methylene chloride containing N-hydroxybenzotriazole (98.0 mg, 0.725 mmol) and EDC (2.09 g, 13.5 mmole) was added N-methylpiperazine (4, 1.45 g, 14.5 mmole) and the reaction mixture was stirred at room temperature overnight. The reaction mixture was evaporated to dryness and the product purified by column using 5% methanol in methylene chloride to give the required ester 5 as a semi solid (1.89 g, 67%). This was further purified by triturating with isopropyl ether followed by re-crystallization with a mixture of ethyl acetate/Hexane to give a white crystalline material of 5 (LB-107)(1.10 g, yield: 39%, mp 108-109° C.). The mother liquor was concentrated and saved for future recrystallization. $^1$H NMR (CDCl$_3$) δ 1.50 (m, 2H), 1.83 (m, 2H), 2.30-2.44 (m, 7H), 2.94 (d, J=9.6 Hz, 1H), 3.10 (d, J=9.6 Hz, 1H), 3.50 (m, 3H), 3.71 (m, 4H), 4.90 (m, 2H), ESMS: 282.

Example 2

Protein Phosphatase 2A Inhibitors

The compounds used in the method of the present invention are protein phosphatase 2A (PP2A) inhibitors (Lu et al., 2009; U.S. Pat. No. 7,998,957 B2). Compounds LB-100 and LB-102 are inhibitors of PP2A in vitro in human cancer cells and in xenografts of human tumor cells in mice when given parenterally in mice. These compounds inhibit the growth of cancer cells in mouse model systems. It has also been shown that another structural homolog of these compounds, LB-107, is active when given orally to mice.

Human cells from patients diagnosed with Type 2 Diabetes are treated with LB100, LB102 or LB107.

The structure of LB100 is:

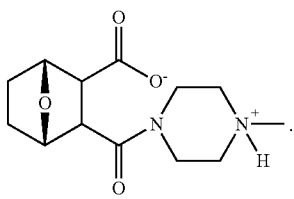

The structure of LB102 is:

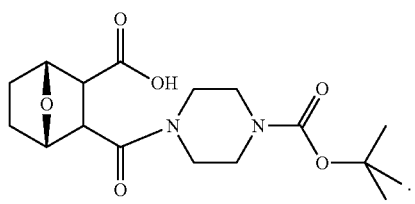 [SMILES: CC(C)(C)OC(=O)N1CCN(C(=O)C2C(C(=O)O)[C@H]3CC[C@@H]2O3)CC1]

The structure of LB107 is:

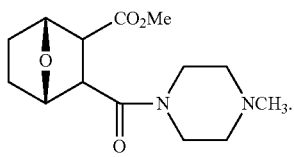 [SMILES: COC(=O)C1C(C(=O)N2CCN(C)CC2)[C@@H]2CC[C@H]1O2]

Example 3

Reduced Dephosphorylation and Inactivation of Akt

Compounds LB-100, LB-102, LB-107, and other homologs of LB-100 disclosed herein increase phosphorylation of Akt in mammalian cells, including, but not limited to, fat cells, liver cells, muscle cells, endothelial cells hepatocytes, or pancreatic islet O-cells. Compounds LB-100, LB-102 and LB-107 and other homologs of LB-100 disclosed herein reduce dephosphorylation and inactivation of Akt by protein phosphatase 2A (PP2A) in mammalian cells, including, but not limited to, fat cells, liver cells, muscle cells, endothelial cells hepatocytes, or pancreatic islet β-cells. Compounds LB-100, LB-102 and LB-107 and other homologs of LB-100 disclosed herein increase activation of Akt by protein phosphatase 2A (PP2A) in mammalian cells, including, but not limited to, fat cells, liver cells, muscle cells, endothelial cells hepatocytes, or pancreatic islet β-cells.

Example 4

Insulin Resistance

Compounds LB-100, LB-102, LB-107 and other homologs of LB-100 disclosed herein increase insulin sensitivity in in human patients diagnosed with Type 2 Diabetes. Compounds LB-100, LB-102, LB-107 and other homologs of LB-100 disclosed herein reduce insulin resistance in human patients diagnosed with Type 2 Diabetes.

Example 5

Vascular Injury

Compounds LB-100, LB-102, LB-107 and other homologs of LB-100 disclosed herein reduce Type 2 Diabetes related vascular injury in the liver, muscle, retina and pancreas and reduce Type 2 Diabetes related vascular injury caused by disruption of the endothielial barrier in human patients diagnosed with Type 2 Diabetes.

Example 6

Other Symptoms of Type 2 Diabetes

Compounds LB-100, LB-102, LB-107 and other homologs of LB-100 disclosed herein reduce complications associated with or caused by Type 2 Diabetes. Compounds LB-100, LB-102, LB-107 and other homologs of LB-100 disclosed herein reduce the effects of other dysfunctions associated with or caused by Type 2 Diabetes including, but not limited to, atherosclerosis low glucose tolerance, dyslipidemia, hyperlipidemia, hypertriglyceridemia, and hypercholesterolemia.

Discussion

Type 2 diabetes is one of the major medical problems facing populations throughout the world. In the United States, approximately 15% of the adult population is believed to have type 2 diabetes. This percentage of incidence is steadily increasing. It has recently been reported that even children are now being diagnosed with type 2 diabetes, a phenomenon that has almost been unheard of in the past. In type 2 diabetes the ability of insulin to decrease glucose production is impaired and overcoming this insulin resistance is a major goal in type 2 diabetes.

Ugi (Ugi et al, 2002) studied the serine/threonine phosphorylation on the metabolic actions of insulin. They obtained data suggesting that PP2A may directly dephosphorylate and thereby inactivate the enzymes Akt and protein kinase C λ resulting in a decrease in glucose transport stimulated by insulin in fat cells in culture. Their results show PP2A as a negative regulator of metabolic signaling by insulin.

It has been reported that in genetically insulin-resistant Zucker Diabetic Fatty (ZDF) rats, PP2A activity is increased in liver, muscle, and fat tissue (Galbo et al, 2011). It has also been reported that rat liver cells exposed to palmitate, a fatty acid, PP2A activity is increased (Galbo et al, 2011). These results lead to the conclusion that free fatty acids may be responsible for a selective reduction of insulin effects upon glucose metabolism in the liver by increased PP2A activity. Inhibition of PP2A activity with known PP2A inhibitors, okadaic acid and cantharidin, reversed the impairment of insulin activity (Galbo et al, 2011). This reversal appeared to be the result of activation of Akt, an enzyme known to be dephosphorylated by PP2A. The PP2A inhibitors of the present method have analogous effects to the PP2A inhibitors okadaic acid and cantharidin with regards to reversing the impairment of insulin activity.

Kowluru (Kowluru et al, 2012) has reviewed hyperactivation of PP2A in models of glucolipotoxicity and diabetes. PP2A function is a novel therapeutic target for the prevention of deleterious effects of diabetes on a number of tissues including liver, muscle, retina and pancreatic islet cells. Inhibition of PP2A activity might reduce the toxic effects of abnormal signaling pathways and restore normal cell function in diabetes and other disorders of metabolism.

In addition to the use of inhibitors of PP2A to ameliorate diabetes, activation of PP2A occurs under the stress of cytokine exposure in addition to conditions of hyperglycemia and hyperlipidemia result in increased PP2A activity in skeletal muscle microvascular endothelial cells disrupting the endothelial barrier (Wu et al., 2009). Indeed, Zhou (Zhou et al, 2012) showed that ascorbic acid and okadaic acid, a known inhibitor of PP2A prevent the induction of endothelial barrier injury by lipopolysaccharide and interferon gamma. These observations serve to link mechanisms resulting in the toxicity of diabetes to the microvasculature and to endotoxic shock. The PP2A inhibitors of the present method have analogous effects to the PP2A inhibitors okadaic acid and cantharidin with regards to prevention the induction of endothelial barrier injury by lipopolysaccharide and interferon gamma.

Kowluru (Kowluru et al. 2012) indicates that increased PP2A is the mechanism underlying insulin resistant diabetes and in the vascular injury that occurs particularly in liver, muscle, retina, and pancreatic islet cells. It appears that increased fatty acids increase the concentration of PP2A and that the PP2A in turn cause insulin resistance and also vascular injury including disruption of the endothelial barrier. Disruption of the endothelial barrier is also a major contributor to tissue injury following ischemia of any type including myocardial infarction, stroke due to vascular occlusion, cardiac ischemia during open heart surgery (being on the pump) and the resultant reperfusion injury resulting when patients are taken off the pump. An inhibitor of PP2A, okadaic acid, prevents the induction of endothelial barrier dysfunction by lipopolysaccharide and interferon gamma (Zhou et al, 2012).

Endothelial disfunction is a primary cause of atherosclerosis, which is associated with Type 2 Diabetes (Ladurner et al. 2012). Ascorbate improves endothelial barrier function in a model of sepsis by inhibition of PP2A activation (Han et al. 2010) and increased production of nitric oxide (May et al, 2011). Ladurner also showed that these effects on endothelial dysfunction are reduced by a reduction by PP2A activity.

Du (Du et al. 2010) had shown that high glucose levels activate PP2A which contributes to death of endothelial cells, a phenomenon inhibited in part by inhibition of PP2A activation.

As early as 2002, Hojlund (Hojlund et al. 2002) showed in muscle biopsies of type 2 diabetes patients and control subjects that insulin decreased the activity of PP2A in controls but not in type 2 diabetic patients. They concluded that impaired down-regulation of PP2A by insulin may be a marker for insulin resistance and contribute to the pathogenesis of type 2 diabetes.

LB-100 and homologs reduce insulin resistance that occurs in Type II diabetes. Disclosed herein is that PP2A inhibitors are effective in treating insulin resistance, Type 2 Diabetes and disorders related to Type 2 Diabetes. Experimental compounds LB-100 and LB-102 and there analogs disclosed herein are inhibitors of PP2A in vitro in human cancer cells and in xenografts of human tumor cells in mice when given parenterally in mice. These compounds inhibit the growth of cancer cells in mouse model systems. We have also shown that another structural homolog of these compounds, LB-107, is active when given orally to mice. LB-100 is entering clinical trials as a potential agent for enhancing the effectiveness of certain anticancer agents. Toxicity studies in rats and dogs have indicated that LB-100 can be administered intravenously at doses known to reduce PP2A activity in the tissue of animals without undue toxicity.

REFERENCES

Du, Y. et al. (2010) PP2A contributes to endothelial death in high glucose: Inhibition by benfotiamine. Am J Physiol Regul Integr Comp Physiol 299:R1610-R1617.

Galbo, T. et al. (2011) Free fatty acid-induced PP2A hyperactivity selectively impairs hepatic insulin action on glucose metabolism. PLoS ONE 6(11): 1-9.

Han, M. et al. (2010) Ascorbate protects endothelial barrier function during septic insult: Role of protein phosphatase type 2A. Free Radical Biology & Medicine. 48, 128-135.

Kowluru et al. (2009) Hyperactivation of protein phosphatase 2A in models of glucolipo toxicity and diabetes: potential mechanism and functional consequences. Biochemical Pharmacology, In Press.

Ladurner et al. (2012) Ascorbate stimulates endothelial nitric oxide synthese enzyme activity by rapid modulation of its phosphorylation status. Free Radical Biology and Medicine, In Press.

Lu, J. et al. (2009) Inhibition of serine/threonine phosphatase PP2A enhances cancer chemotherapy by blocking DNA damage induced defense mechanisms. PNAS 106 (28):11697-11702.

May, J. M. et al. (2011) Nitric oxide mediates tightening of the endothelial barrier by ascorbic acid. Biochemical and Biophysical Research Communications. 404, 701-705.

Ugi, S. et al. (2004) Protein phosphatase 2A negatively regulates insulin's metabolic signaling pathway by inhibiting Akt (protein kinase B) activity in 3T3-L1 adipocytes. Molecular and Cellular Biology 24:8778-8789.

Wu, F. and Wilson, J. X. (2009) Peroxynitrite-dependent activation of protein phosphatase type 2A mediates microvascular endothelial barrier dysfunction. Cardiovascular Research. 81:38/45.

Wu, et al. (2007) Activation or Protein Phosphatase 2A by Palmitate Inhibits AMP-activated Protein Kinase. The Journal of Biological Chemisty. 282, 13, 9777-9788.

Zhou, G. et al. (2012) Ascorbate protects against vascular leakage in cecal ligation and puncture-induced septic peritonitis. American J Physiol Regul Integr Comp Physiol 302:409-416.

What is claimed is:

1. A method of reducing complications associated with Type 2 Diabetes in a subject afflicted with Type 2 Diabetes comprising administering to the subject a therapeutically effective amount of a protein phosphatase 2A inhibitor having the structure:

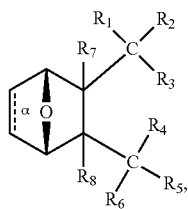

wherein
bond α is present or absent;
$R_1$ and $R_2$ is each independently H, O$^-$ or OR$_9$,
 where $R_9$ is H, alkyl, alkenyl, alkynyl or aryl,
 or $R_1$ and $R_2$ together are =O;
$R_3$ and $R_4$ are each different, and each is OH, O$^-$, OR$_9$, OR$_{10}$, O(CH$_2$)$_{1-6}$R$_9$, SH, S$^-$, SR$_9$,

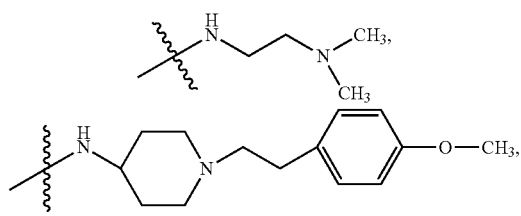

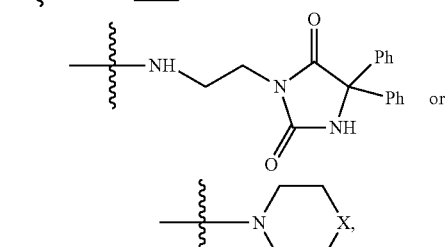

where X is O, S, NR$_{10}$, or N$^+$R$_{10}$R$_{10}$,
 where each R$_{10}$ is independently H, alkyl, alkenyl, alkynyl, aryl, substituted aryl where the substituent is other than chloro when $R_1$ and $R_2$ are =O,

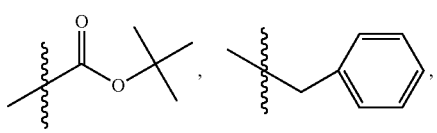

—CH$_2$CN, —CH$_2$CO$_2$R$_{11}$, —CH$_2$COR$_{11}$, —NHR$_{11}$ or —NH$^+$(R$_{11}$)$_2$,
 wherein each R$_{11}$ is independently alkyl, alkenyl or alkynyl, or H;
$R_5$ and $R_6$ is each independently H, OH, or $R_5$ and $R_6$ taken together are =O;
$R_7$ and $R_8$ is each independently H, F, Cl, Br, SO$_2$Ph, CO$_2$CH$_3$, or SR$_{12}$,
 where R$_{12}$ is H, alkyl, alkenyl, alkynyl or aryl; and
each occurrence of alkyl, alkenyl, or alkynyl is branched or unbranched, unsubstituted or substituted,
or a salt, enantiomer or zwitterion of the compound, so as to thereby reduce the complications associated with Type 2 Diabetes in the subject,
wherein the complications associated with Type 2 Diabetes in the subject are selected from atherosclerosis, low glucose tolerance, dyslipidemia, hyperlipidemia, hypertriglyceridemia, and hypercholesterolemia.

2. A method of reducing a complication associated with Type 2 Diabetes in a subject afflicted with Type 2 Diabetes comprising administering to the subject a therapeutically effective amount of a protein phosphatase 2A inhibitor having the structure:

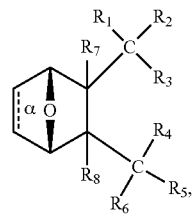

wherein
bond α is present or absent;
$R_1$ and $R_2$ is each independently H, O$^-$ or OR$_9$,
 where $R_9$ is H, alkyl, alkenyl, alkynyl or aryl,
 or $R_1$ and $R_2$ together are =O;
$R_3$ and $R_4$ are each different, and each is OH, O$^-$, OR$_9$, OR$_{10}$, O(CH$_2$)$_{1-6}$R$_9$, SH, S$^-$, SR$_9$,

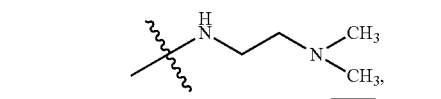

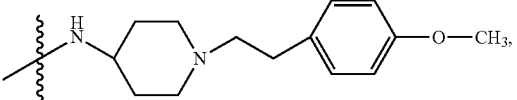

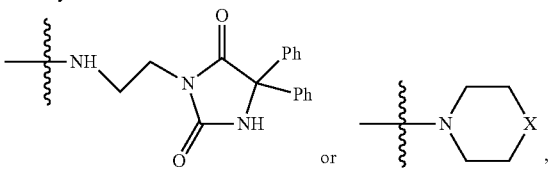

where X is O, S, NR$_{10}$, or N$^+$R$_{10}$R$_{10}$,
 where each R$_{10}$ is independently H, alkyl, alkenyl, alkynyl, aryl, substituted aryl where the substituent is other than chloro when $R_1$ and $R_2$ are =O,

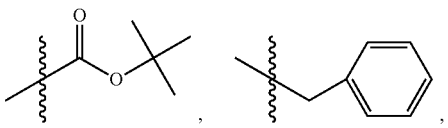

—CH$_2$CN, —CH$_2$CO$_2$R$_{11}$, —CH$_2$COR$_{11}$, —NHR$_{11}$ or —NH$^+$(R$_{11}$)$_2$, wherein each $R_{11}$ is independently alkyl, alkenyl or alkynyl, or H;
$R_5$ and $R_6$ is each independently H, OH, or $R_5$ and $R_6$ taken together are =O;
$R_7$ and $R_8$ is each independently H, F, Cl, Br, $SO_2Ph$, $CO_2CH_3$, or $SR_{12}$,
where $R_{12}$ is H, alkyl, alkenyl, alkynyl or aryl; and
each occurrence of alkyl, alkenyl, or alkynyl is branched or unbranched, unsubstituted or substituted,
or a salt, enantiomer or zwitterion of the compound, so as to thereby reduce the complication associated with Type 2 Diabetes in the subject,
wherein the complication associated with Type 2 Diabetes in the subject is vascular injury.

3. The method of claim 1, wherein the protein phosphatase 2A inhibitor has the structure

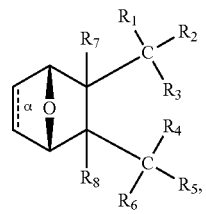

wherein
bond α is present or absent;
$R_1$ and $R_2$ is each independently H, O⁻ or $OR_9$,
where $R_9$ is H, alkyl, alkenyl, alkynyl or aryl,
or $R_1$ and $R_2$ together are =O;
$R_3$ and $R_4$ are each different, and each is OH, O⁻, $OR_9$, SH, S⁻, $SR_9$,

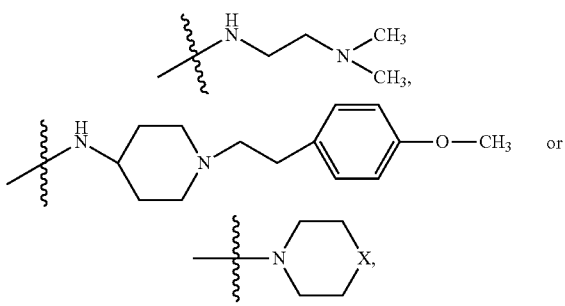

where X is O, S, $NR_{10}$, or $N^+R_{10}R_{10}$,
where each $R_{10}$ is independently H, alkyl, alkenyl, alkynyl, aryl, substituted aryl where the substituent is other than chloro when $R_1$ and $R_2$ are =O,

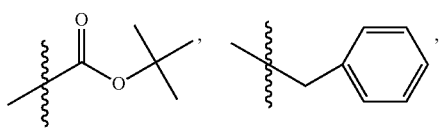

—$CH_2CN$, —$CH_2CO_2R_{11}$, —$CH_2COR_{11}$, —$NHR_{11}$ or —$NH^+(R_{11})_2$,
where each $R_{11}$ is independently alkyl, alkenyl alkynyl, or H;
$R_5$ and $R_6$ is each independently H, OH, or $R_5$ and $R_6$ taken together are =O;
$R_7$ and $R_8$ is each independently H, F, Cl, Br, $SO_2Ph$, $CO_2CH_3$, or $SR_{12}$,
where $R_{12}$ is H, aryl, alkyl, alkenyl or alkynyl; and
each occurrence of alkyl, alkenyl, or alkynyl is branched or unbranched, unsubstituted or substituted,
or a salt, enantiomer or zwitterion of the compound.

4. The method of claim 2, wherein the protein phosphatase 2A inhibitor has the structure

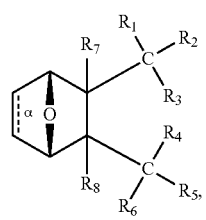

wherein
bond α is present or absent;
$R_1$ and $R_2$ is each independently H, O⁻ or $OR_9$,
where $R_9$ is H, alkyl, alkenyl, alkynyl or aryl,
or $R_1$ and $R_2$ together are =O;
$R_3$ and $R_4$ are each different, and each is OH, O⁻, $OR_9$, SH, S⁻, $SR_9$,

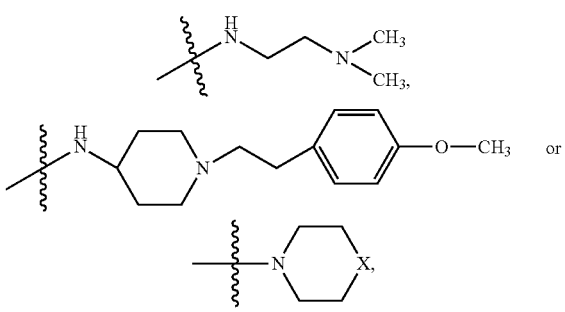

where X is O, S, $NR_{10}$, or $N^+R_{10}R_{10}$,
where each $R_{10}$ is independently H, alkyl, alkenyl, alkynyl, aryl, substituted aryl where the substituent is other than chloro when $R_1$ and $R_2$ are =O,

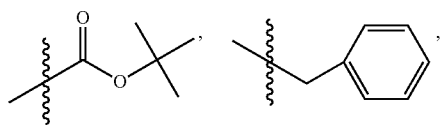

—$CH_2CN$, —$CH_2CO_2R_{11}$, —$CH_2COR_{11}$, —$NHR_{11}$ or —$NH^+(R_{11})_2$,
where each $R_{11}$ is independently alkyl, alkenyl alkynyl, or H;
$R_5$ and $R_6$ is each independently H, OH, or $R_5$ and $R_6$ taken together are =O;
$R_7$ and $R_8$ is each independently H, F, Cl, Br, $SO_2Ph$, $CO_2CH_3$, or $SR_{12}$,
where $R_{12}$ is H, aryl, alkyl, alkenyl or alkynyl; and
each occurrence of alkyl, alkenyl, or alkynyl is branched or unbranched, unsubstituted or substituted,
or a salt, enantiomer or zwitterion of the compound.

5. The method of claim 3,
wherein
R₁ and R₂ together are =O;
R₃ is O⁻ or OR₉,
  where R₉ is H, methyl, ethyl or phenyl;
R₄ is

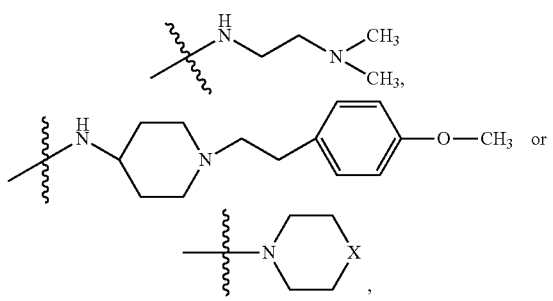

where X is O, S, NR₁₀, or N⁺R₁₀R₁₀,
  where each R₁₀ is independently H, alkyl, alkenyl, alkynyl, aryl, substituted aryl where the substituent is other than chloro,

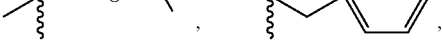

—CH₂CN, —CH₂CO₂R₁₁, —CH₂COR₁₁, —NHR₁₁ or —NH⁺(R₁₁)₂,
  where R₁₁ is alkyl, alkenyl or alkynyl, or H;
R₅ and R₆ taken together are =O; and
R₇ and R₈ is each independently H, F, Cl, Br, SO₂Ph, CO₂CH₃, or SR₁₂,
  where R₁₂ is an alkyl, alkenyl or alkynyl; and
each occurrence of alkyl, alkenyl, or alkynyl is branched or unbranched, unsubstituted or substituted,
or a salt, enantiomer or zwitterion of the compound.

6. The method of claim 4,
wherein
R₁ and R₂ together are =O;
R₃ is O⁻ or OR₉,
  where R₉ is H, methyl, ethyl or phenyl;
R₄ is

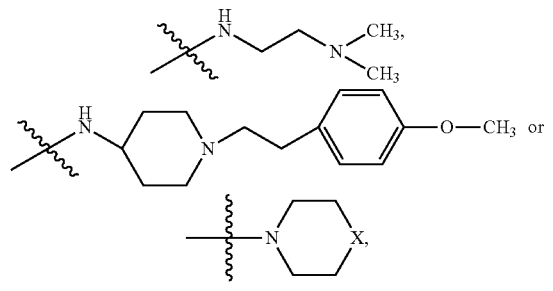

where X is O, S, NR₁₀, or N⁺R₁₀R₁₀,
  where each R₁₀ is independently H, alkyl, alkenyl, alkynyl, aryl, substituted aryl where the substituent is other than chloro,

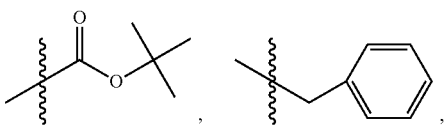

—CH₂CN, —CH₂CO₂R₁₁, —CH₂COR₁₁, —NHR₁₁ or —NH⁺(R₁₁)₂,
  where R₁₁ is alkyl, alkenyl or alkynyl, or H;
R₅ and R₆ taken together are =O; and
R₇ and R₈ is each independently H, F, Cl, Br, SO₂Ph, CO₂CH₃, or SR₁₂,
  where R₁₂ is an alkyl, alkenyl or alkynyl; and
each occurrence of alkyl, alkenyl, or alkynyl is branched or unbranched, unsubstituted or substituted,
or a salt, enantiomer or zwitterion of the compound.

7. The method of claim 5,
wherein R₄ is

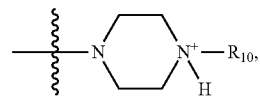

where R₁₀ is H, alkyl, alkenyl, alkynyl, aryl, substituted aryl where the substituent is other than chloro when R₁ and R₂ are =O,

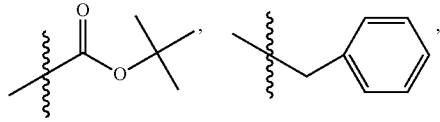

—CH₂CN, —CH₂CO₂R₁₁, —CH₂COR₁₁, —NHR₁₁ or —NH⁺(R₁₁)₂,
  where R₁₁ is H or alkyl; and
each occurrence of alkyl, alkenyl, or alkynyl is branched or unbranched, unsubstituted or substituted,
or a salt, enantiomer or zwitterion of the compound.

8. The method of claim 6,
wherein R₄ is

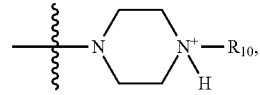

where R₁₀ is H, alkyl, alkenyl, alkynyl, aryl, substituted aryl where the substituent is other than chloro when R₁ and R₂ are =O,

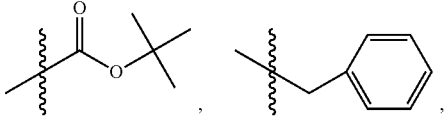

—CH$_2$CN, —CH$_2$CO$_2$R$_{11}$, —CH$_2$COR$_{11}$, —NHR$_{11}$ or —NH$^+$(R$_{11}$)$_2$, where R$_{11}$ is H or alkyl; and each occurrence of alkyl, alkenyl, or alkynyl is branched or unbranched, unsubstituted or substituted, or a salt, enantiomer or zwitterion of the compound.

9. The method of claim 7,
wherein R$_4$ is

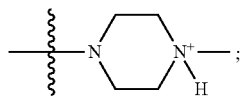

or
wherein R$_4$ is

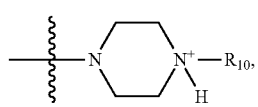

where R$_{10}$ is

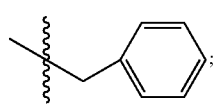

or
wherein R$_4$ is

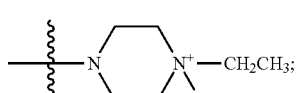

or
wherein R$_4$ is

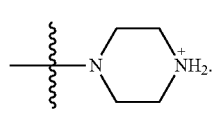

10. The method of claim 8,
wherein R$_4$ is

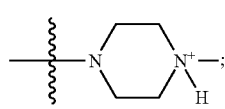

or
wherein R$_4$ is

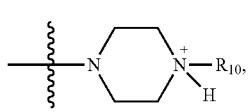

where R$_{10}$ is

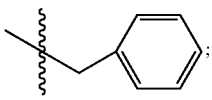

or
where R$_4$ is

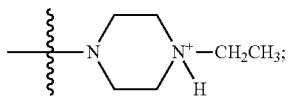

or
wherein R$_4$ is

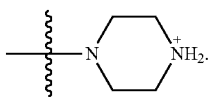

11. The method of claim 3, wherein the protein phosphatase 2A inhibitor has the structure

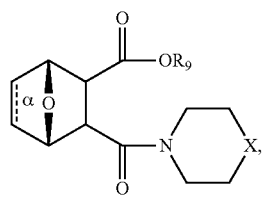

wherein bond α is present or absent;

R$_9$ is present or absent and when present is H, alkyl, alkenyl, alkynyl or phenyl; and X is O, NR$_{10}$, or N$^+$R$_{10}$R$_{10}$, where each R$_{10}$ is independently H, alkyl, alkenyl, alkynyl, aryl, substituted aryl where the substituent is other than chloro,

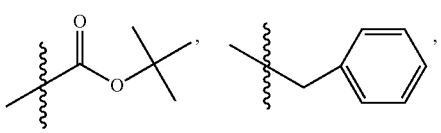

—CH$_2$CN, —CH$_2$CO$_2$R$_{11}$, or —CH$_2$COR$_{11}$, where R$_{11}$ is H or alkyl; and each occurrence of alkyl, alkenyl, or alkynyl is branched or unbranched, unsubstituted or substituted, or a salt, zwitterion, or enantiomer of the compound.

12. The method of claim 4, wherein the protein phosphatase 2A inhibitor has the structure

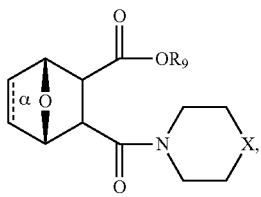

wherein bond α is present or absent;

R$_9$ is present or absent and when present is H, alkyl, alkenyl, alkynyl or phenyl; and X is O, NR$_{10}$, or N$^+$R$_{10}$R$_{10}$, where each R$_{10}$ is independently H, alkyl, alkenyl, alkynyl, aryl, substituted aryl where the substituent is other than chloro,

—CH$_2$CN, —CH$_2$CO$_2$R$_{11}$, or —CH$_2$COR$_{11}$, where R$_{11}$ is H or alkyl; and each occurrence of alkyl, alkenyl, or alkynyl is branched or unbranched, unsubstituted or substituted, or a salt, zwitterion, or enantiomer of the compound.

13. The method of claim 11, wherein the protein phosphatase 2A inhibitor has the structure

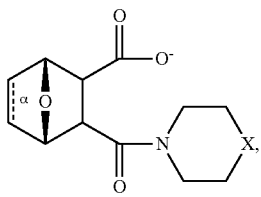

wherein bond α is present or absent;

X is O or NH$^+$R$_{10}$, where R$_{10}$ is H, alkyl, alkenyl, alkynyl, aryl, substituted aryl where the substituent is other than chloro,

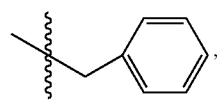

—CH$_2$CN, —CH$_2$CO$_2$R$_{11}$, or —CH$_2$COR$_{11}$, where R$_{11}$ is H or alkyl; and each occurrence of alkyl, alkenyl, or alkynyl is branched or unbranched, unsubstituted or substituted, or a salt, enantiomer or zwitterion of the compound.

14. The method of claim 12, wherein the protein phosphatase 2A inhibitor has the structure

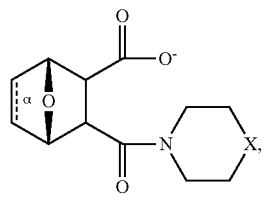

wherein bond α is present or absent;

X is O or NH$^+$R$_{10}$, where R$_{10}$ is H, alkyl, alkenyl, alkynyl, aryl, substituted aryl where the substituent is other than chloro,

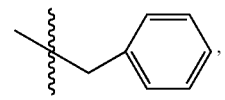 [SMILES: *Cc1ccccc1 ; ","]

—CH$_2$CN, —CH$_2$CO$_2$R$_{11}$, or —CH$_2$COR$_{11}$, where R$_{11}$ is H or alkyl; and each occurrence of alkyl, alkenyl, or alkynyl is branched or unbranched, unsubstituted or substituted, or a salt, enantiomer or zwitterion of the compound.

15. The method of claim 3, wherein the protein phosphatase 2A inhibitor has the structure

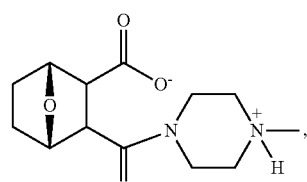

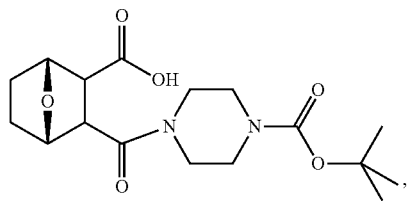

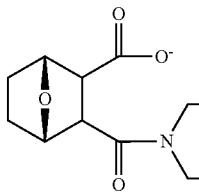

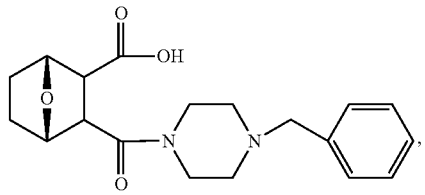

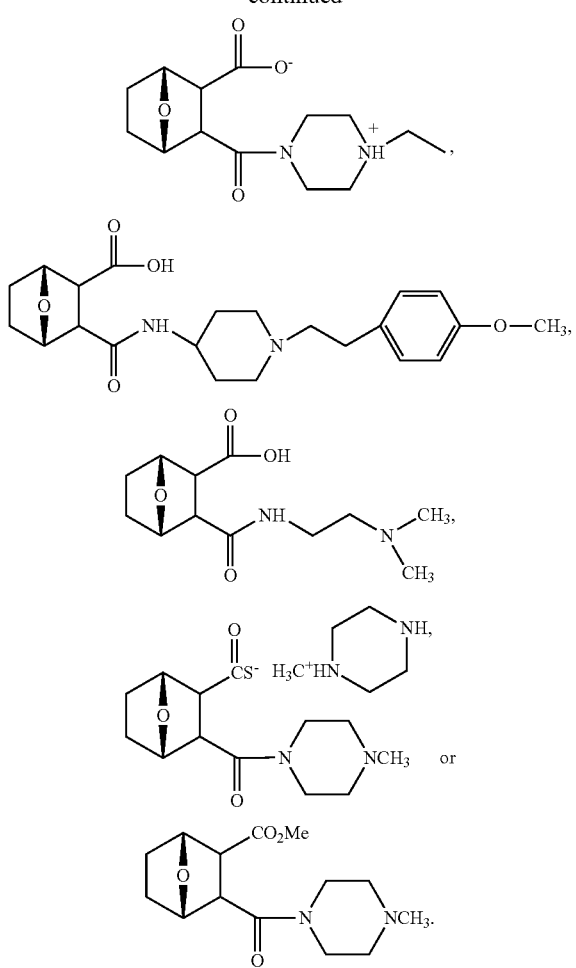
16. The method of claim 4, wherein the protein phosphatase 2A inhibitor has the structure
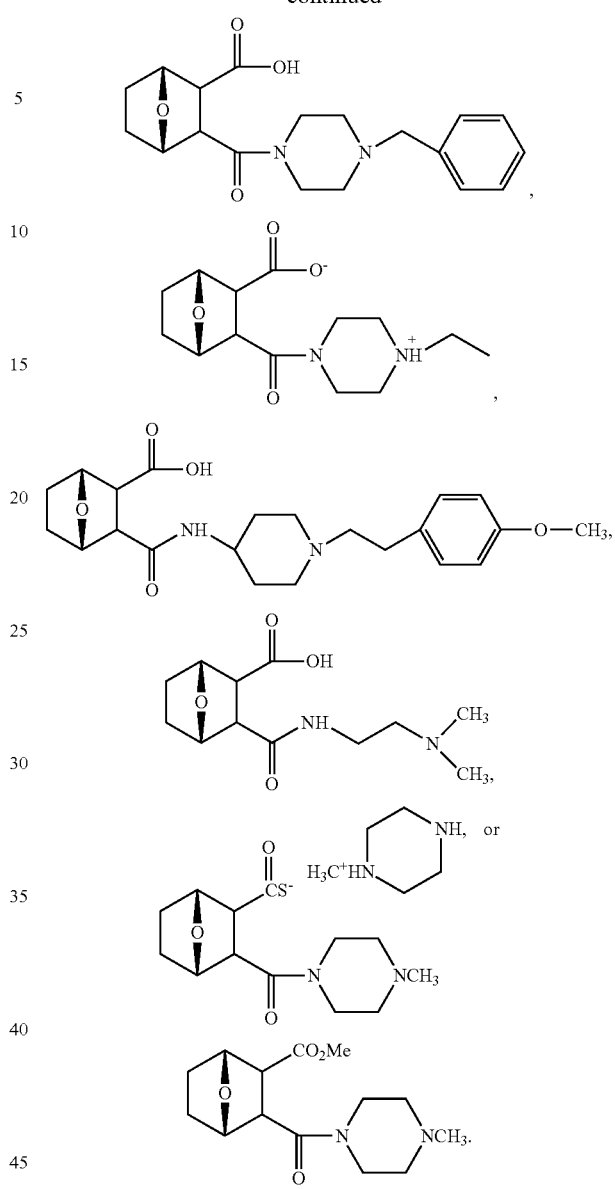
17. The method of claim 3, wherein the protein phosphatase 2A inhibitor has the structure -continued
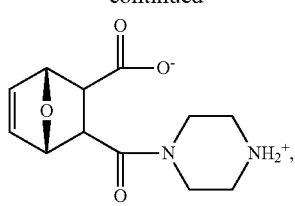
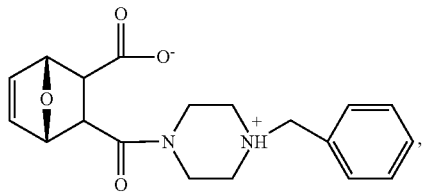
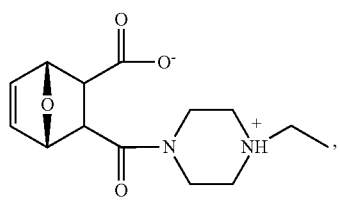
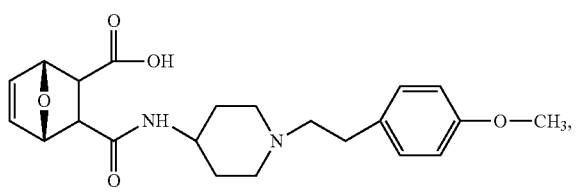
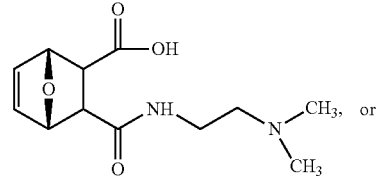
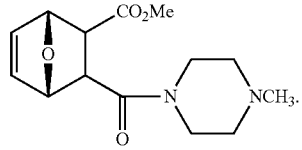
18. The method of claim 4, wherein the protein phosphatase 2A inhibitor has the structure
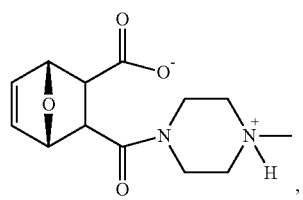
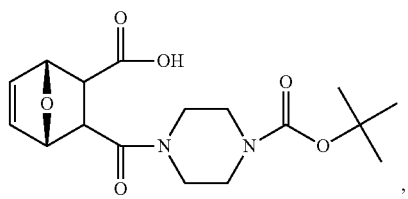
-continued
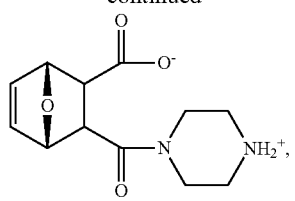
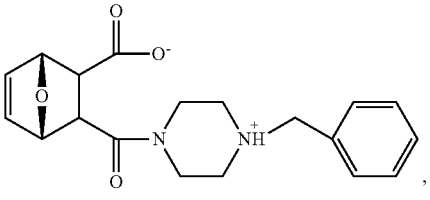
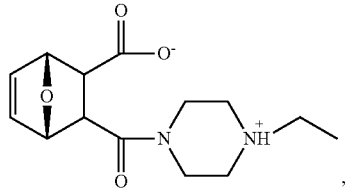
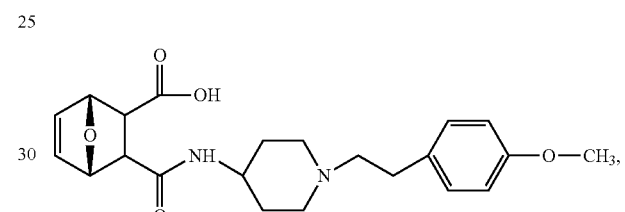
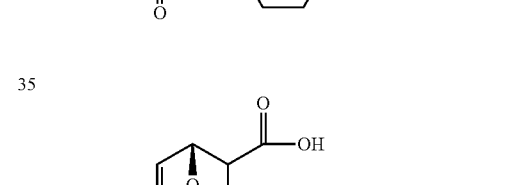
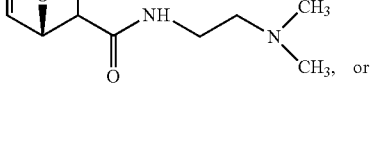
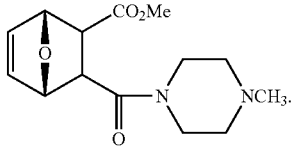
19. The method of claim 3, wherein the protein phosphatase 2A inhibitor has the structure
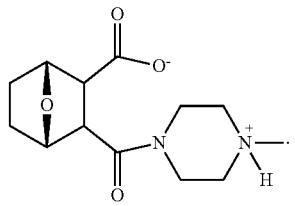
20. The method of claim 4, wherein the protein phosphatase 2A inhibitor has the structure

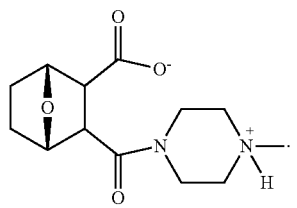
* * * * *